United States Patent [19]
Castro Pineiro et al.

[11] Patent Number: 6,140,347
[45] Date of Patent: Oct. 31, 2000

[54] AZETIDINE, PYRROLIDINE AND PIPERIDINE DERIVATIVES AS 5-HT RECEPTOR AGONISTS

[75] Inventors: Jose Luis Castro Pineiro, Bishops Stortford; Andrew Madin, Sawbridgeworth; Joseph George Neduvelil, Barnet; Graham Andrew Showell, Welwyne Garden City; Leslie Joseph Street, Harlow; Monique Bodil Van Niel, Welwyn Garden City, all of United Kingdom

[73] Assignee: Merck Sharp & Dohme Ltd., Hoddesdon, United Kingdom

[21] Appl. No.: 09/171,208

[22] PCT Filed: Apr. 24, 1997

[86] PCT No.: PCT/GB97/01137

§ 371 Date: Oct. 14, 1998

§ 102(e) Date: Oct. 14, 1998

[87] PCT Pub. No.: WO97/42189

PCT Pub. Date: Nov. 13, 1997

[30] Foreign Application Priority Data

May 3, 1996 [GB] United Kingdom ............ 9609374

[51] Int. Cl.[7] ............ A61K 31/445; A61K 31/415; C07D 401/14
[52] U.S. Cl. ............ 514/323; 514/383; 546/202; 548/266.4; 548/466; 548/468
[58] Field of Search ............ 546/202; 548/266.4, 548/466, 468; 514/323, 383

[56] References Cited

U.S. PATENT DOCUMENTS 5,567,726  10/1996  Baker et al. ............ 514/383
5,780,437  7/1998  Goulet ............ 514/19

FOREIGN PATENT DOCUMENTS 464558    1/1992   European Pat. Off. .
548813    6/1993   European Pat. Off. .
WO 91/18897  12/1991  WIPO .
93/11106  6/1993  WIPO .
WO 95/32196  11/1995  WIPO .
WO 96/04269  2/1996  WIPO .
WO 96/16056  5/1996  WIPO .

OTHER PUBLICATIONS

Glen et al. "Computer aided design and synthesis of 5–substituted tryptamines . . . " J. Med. Chem. v. 38, p. 3566–80, 1995.
Rubini et al. "Synthesis of isosteric methylene–oxy psudodipeptide analogues . . . " Tetrahedron vo. 42, p. 6039–45, 1986.
International Search Report Aug. 5, 1997.

*Primary Examiner*—Ceila Chang
*Attorney, Agent, or Firm*—James L. McGinnis; David L. Rose

[57] ABSTRACT

A class of compounds of formula (I) wherein Z, E, Q, T, U, V, W, M, $R^1$, $R^7$ and $R^8$ are as defined herein; are selective agonists of $5\text{-HT}_1$-like receptors, being potent agonists of the human $5\text{-HT}_{1D\alpha}$ receptor subtype whilst possessing at least a 10-fold selective affinity for the $5\text{-HT}_{1D\alpha}$ receptor subtype relative to the $5\text{-HT}_{1D\beta}$ subtype; they are therefore useful in the treatment and/or prevention of clinical conditions, in particular migraine and associated disorders, for which a subtype-selective agonist of $5\text{-HT}_{1D}$ receptors is indicated, whilst eliciting fewer side-effects, notably adverse cardiovascular events, than those associated with non-subtype-selective $5\text{-HT}_{1D}$ receptor agonists.

(I)

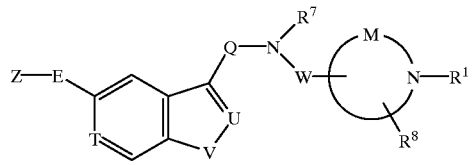

9 Claims, No Drawings

AZETIDINE, PYRROLIDINE AND PIPERIDINE DERIVATIVES AS 5-HT RECEPTOR AGONISTS

This application is a 371 of PCT/GB97/01137 filed Apr. 24, 1997.

The present invention relates to a class of substituted azetidine, pyrrolidine and piperidine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted azetidine, pyrrolidine and piperidine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of the substituted azetidine, pyrrolidine and piperidine derivatives provided by the present invention.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the substituted azetidine, pyrrolidine and piperidine derivatives provided by the present invention.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

WO-A-95/32196, WO-A-96/04269 and WO-A-96/04274 describe various classes of heterocyclic compounds as alpha subtype-selective agonists of the human 5-HT$_{1D}$ receptor. However, there is no disclosure or suggestion in any of these publications of the substituted azetidine, pyrrolidine and piperidine derivatives provided by the present invention.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover, the compounds in accordance with this invention possess interesting properties in terms of their efficacy and/or bioavailability.

The present invention provides a compound of formula I, or a salt or prodrug thereof:

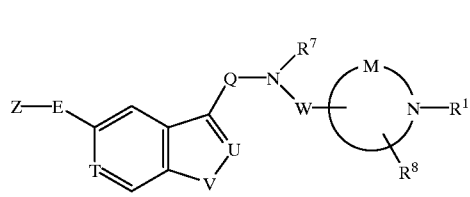

(I)

wherein

Z represents hydrogen, halogen, cyano, nitro, trifluoromethyl, —OR$^5$—OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —$NR^5CO_2R^6$, —$NR^5SO_2R^6$, —$COR^5$, —$CO_2R^5$, —$CONR^5R^6$, or a group of formula (a), (b), (c) or (d):

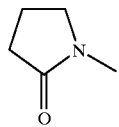

(a)

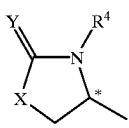

(b)

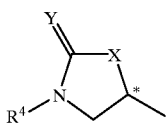

(c)

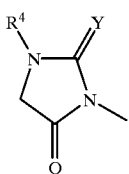

(d)

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 4 carbon atoms, optionally substituted in any position by one or more substituents selected from fluoro and hydroxy;

T represents nitrogen or CH;

U represents nitrogen or C—$R^2$;

V represents oxygen, sulphur or N—$R^3$;

W represents a chemical bond or a straight or branched alkylene chain containing from 1 to 4 carbon atoms;

M represents the residue of an azetidine, pyrrolidine or piperidine ring;

$R^1$ represents $C_{3-7}$ cycloalkyl($C_{1-6}$)alkyl, aryl($C_{1-6}$)alkyl or heteroaryl($C_{1-6}$)alkyl, any of which groups may be optionally substituted;

$R^2$, $R^3$, $R^4$ and $R^7$ independently represent hydrogen or $C_{1-6}$ alkyl;

$R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring; and $R^8$ represents hydrogen or hydroxy.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$) alkyl, $C_{3-7}$ heterocycloalkyl, heteroaryl, heteroaryl($C_{1-6}$) alkyl, $C_{1-6}$ alkoxy, $C_{1-6}$ alkylthio, amino, $C_{1-6}$ alkylamino, di($C_{1-6}$)alkylamino, halogen, cyano and trifluoromethyl.

The group $R^1$ may be optionally substituted by one or more substituents, as also may the groups $R^5$ or $R^6$ where these represent aryl($C_{1-6}$)alkyl or heteroaryl($C_{1-6}$)alkyl. Where $R^1$, $R^5$ or $R^6$ represents aryl($C_{1-6}$)alkyl or heteroaryl ($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyl-tetrazolyl, hydroxy, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N-($C_{1-6}$) alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl ($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

A typical $C_{3-7}$ cycloalkyl($C_{1-6}$)alkyl group is cyclohexylmethyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. For example, the compounds of formula I above wherein Z represents a group of formula (b) or (c) have a chiral centre denoted by the asterisk *, which may accordingly be in the (R) or (S) configuration. It is to be understood that all such isomers and mixtures thereof in any proportion are encompassed within the scope of the present invention.

In particular, where M represents the residue of a pyrrolidine ring, and this ring is attached via the 3-position thereof to the remainder of the molecule, then the absolute stereochemical configuration of the carbon atom at the point of attachment of the pyrrolidine ring to the remainder of the molecule is preferably as depicted in structure IA as follows:

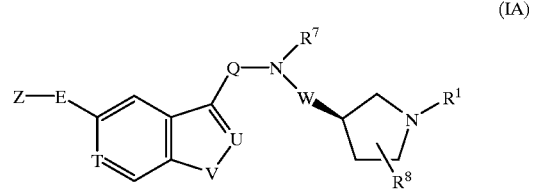

(IA)

wherein Z, E, Q, T, U, V, W, $R^1$, $R^7$ and $R^8$ are as defined above.

Where E, Q and W, which may be the same or different, represent straight or branched alkylene chains, these may be, for example, methylene, ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethylpropylene, 2-fluoropropylene or 2-fluoromethyl-propylene chain Q. Moreover, E and W may each independently represent a chemical bond. Where E represents a chemical bond, the moiety Z is attached directly to the central fused bicyclic heteroaromatic ring system containing the variables T, U and V. Similarly, where W represents a chemical bond, the nitrogen atom of the moiety N—$R^7$ is attached directly to the azetidine, pyrrolidine or piperidine ring of which M is the residue.

Suitably, E represents a chemical bond or a methylene linkage.

Representative alkylene chains for Q include ethylene, propylene, butylene, 2-hydroxypropylene, 2-hydroxymethyl-propylene, 2-fluoropropylene and 2-fluoromethyl-propylene, especially ethylene.

Suitably, W represents a chemical bond, or a methylene or ethylene linkage.

The compound of formula I in accordance with the present invention is suitably an indole, benzofuran or benzthiophene derivative of formula IB, an indazole derivative of formula IC, or a pyrrolo[2,3-c]pyridine derivative of formula ID:

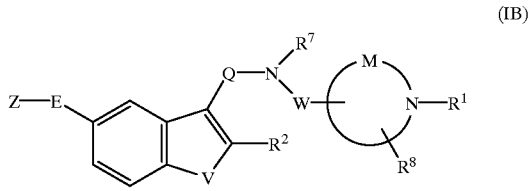

(IB)

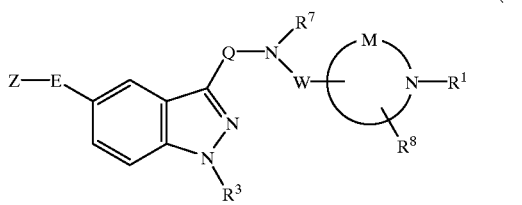

(IC)

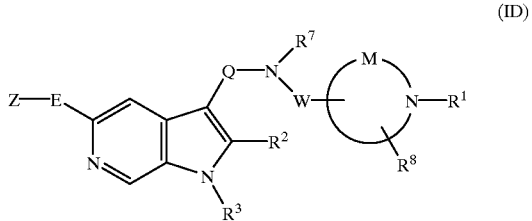

(ID)

wherein Z, E, Q, V, W, M, $R^1$, $R^2$, $R^3$, $R^7$ and $R^8$ are as defined above. Preferably, the compounds according to the invention are indole or pyrrolo[2,3-c]pyridine derivatives of formula IE:

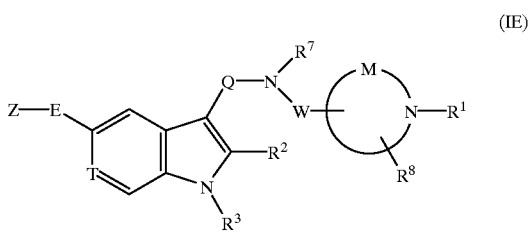

(IE)

wherein Z, E, Q, T, W, M, $R^1$, $R^2$, $R^3$, $R^7$ and $R^8$ are as defined above, in particular wherein $R^2$ and $R^3$ are both hydrogen.

Suitable values for the substituent $R^1$ include cyclohexylmethyl, benzyl, phenylethyl, furylmethyl, thienylmethyl, imidazolylmethyl and pyridinylmethyl, any of which groups may be optionally substituted by one or more substituents selected typically from halogen, cyano, trifluoromethyl, triazolyl, tetrazolyl, $C_{1-6}$ alkyl-tetrazolyl, $C_{1-6}$ alkoxy, amino, di($C_{1-6}$)alkylamino, di($C_{1-6}$)alkylaminomethyl, $C_{2-6}$ alkylcarbonylamino, $C_{2-6}$ alkoxycarbonylamino, N-($C_{1-6}$)alkyl-N-($C_{2-6}$) alkoxycarbonylamino, $C_{1-6}$ alkylsulphonylamino, aminocarbonylamino, aminocarbonyl, $C_{1-6}$ alkylaminocarbonyl, di($C_{1-6}$)alkylaminocarbonyl, aminosulphonyl and $C_{1-6}$ alkylaminosulphonylmethyl.

Particular values of $R^1$ include cyclohexylmethyl, benzyl, fluorobenzyl, chlorobenzyl, cyanobenzyl, trifluoromethyl-benzyl, tetrazolyl-benzyl, methyltetrazolyl-benzyl, methoxybenzyl, aminobenzyl, dimethylaminomethyl-benzyl, acetylamino-benzyl, aminocarbonyl-benzyl, methylaminocarbonyl-benzyl, dimethylaminocarbonyl-benzyl, aminosulphonyl-benzyl, phenylethyl, fluoro-phenylethyl, difluoro-phenylethyl, cyano-phenylethyl, triazolyl-phenylethyl, amino-phenylethyl, dimethylamino-phenylethyl, acetylamino-phenylethyl, methoxy-carbonylamino-phenylethyl, (N-methyl-N-methoxy-carbonyl)amino-phenylethyl, aminocarbonylamino-phenylethyl, furylmethyl, thienylmethyl, imidazolylmethyl, pyridinylmethyl and amino-pyridinylmethyl. Typically, $R^1$ represents cyclohexylmethyl, benzyl, fluorobenzyl, chlorobenzyl or trifluoromethyl-benzyl.

Suitably, $R^2$ and $R^3$ independently represent hydrogen or methyl, especially hydrogen.

Suitably, $R^4$ represents hydrogen or methyl, especially hydrogen.

Suitably, $R^5$ and $R^6$ are independently selected from hydrogen, methyl, ethyl, n-propyl, isopropyl, n-butyl, tert-butyl, trifluoromethyl, phenyl, methylphenyl (especially 4-methylphenyl), benzyl and phenethyl.

Suitably, $R^7$ represents hydrogen, methyl or ethyl, especially methyl or ethyl.

Suitably, $R^8$ represents hydrogen.

Suitably, the substituent Z represents hydrogen, fluoro, cyano, hydroxy, methoxy, ethoxy, benzyloxy, methylamino-carbonyloxy, cyano-methoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylami-nocarbonyl or phenethyl-aminocarbonyl; or a group of formula (a), (b), (c) or (d) as defined above; or an optionally substituted five-membered heteroaromatic ring as specified above.

In a particular embodiment, Z represents $-SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (b) in which $R^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

A particular sub-class of compounds according to the invention is represented by the compounds of formula II, and salts and prodrugs thereof:

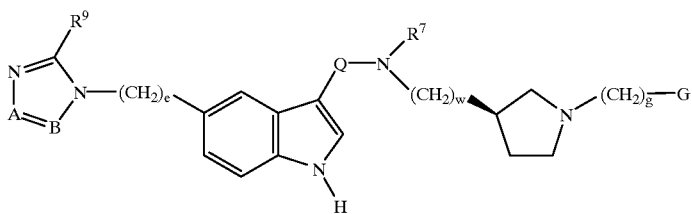

(II)

wherein
e is zero, 1, 2 or 3, preferably zero or 1;
g is 1, 2 or 3, preferably 1 or 2;
q is 2, 3 or 4, preferably 2;
w is zero, 1 or 2, preferably zero;
A represents nitrogen or CH;
B represents nitrogen or C—$R^{10}$;
$R^9$ and $R^{10}$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$) alkylamino, halogen, cyano or trifluoromethyl;
G represents a group of formula (Ga), (Gb), (Gc) or (Gd):

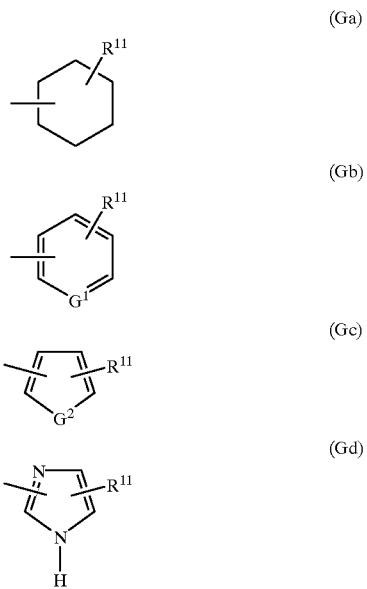

in which
$G^1$ represents CH or nitrogen;
$G^2$ represents oxygen, sulphur, NH or N-methyl; and
$R^{11}$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

Particular values of $R^9$ and $R^{10}$ include hydrogen, methyl, ethyl, benzyl and amino, especially hydrogen.

Particular values of $R^{11}$ include hydrogen, fluoro, chloro, cyano, trifluoromethyl, triazolyl, tetrazolyl, methyltetrazolyl, methoxy, amino, dimethylaminomethyl, acetylamino, aminocarbonylamino, methylaminocarbonyl and aminosulphonyl, especially hydrogen, fluoro, chloro and trifluoromethyl.

In relation to formula II above, the moiety G suitably represents a group of formula (Ga); or a group of formula (Gb) wherein $G^1$ represents CH.

Specific compounds within the scope of the present invention include:
1-benzyl-3-[N-ethyl-N-[2-(5-(1,2,4-triazol-1-ylmethyl)-1H-indol-3-yl)ethyl]amino]methylazetidine;
1-cyclohexylmethyl-3-[N-methyl-N-[2-(5-(1,2,4-triazol-1-ylmethyl)-1H-indol-3-yl)ethyl]amino]methylazetidine;
1-benzyl-3-[N-methyl-N-[2-(5-(1,2,4-triazol-1-ylmethyl)-1H-indol-3-yl)ethyl]amino]methylazetidine;
1-(2-chlorobenzyl)-3-[N-methyl-N-[2-(5-(1,2,4-triazol-1-ylmethyl)-1H-indol-3-yl)ethyl]amino]methylazetidine;
1-(4-fluorobenzyl)-3-[N-methyl-N-[2-(5-(1,2,4-triazol-1-ylmethyl)-1H-indol-3-yl)ethyl]amino]methylazetidine;
1-(2-trifluoromethylbenzyl)-3-[N-methyl-N-[2-(5-(1,2,4-triazol-1-ylmethyl)-1H-indol-3-yl)ethyl]amino] methylazetidine;
1-(2-chloro-6-fluorobenzyl)-3-[N-methyl-N-[2-(5-(1,2,4-triazol-1-ylmethyl)-1H-indol-3-yl)ethyl]amino] methylazetidine;
1-benzyl-3-hydroxy-3-[N-methyl-N-[2-(5-(1,2,4-triazol-1-ylmethyl)-1H-indol-3-yl)ethyl]amino]methylazetidine;
1-benzyl-3-[N-methyl-N-[2-(5-(1,2,4-triazol-1-ylmethyl)-1H-indol-3-yl)ethyl]amino]methylpyrrolidine;
1-benzyl-3-[N-methyl-N-[2-(5-(1,2,4-triazol-1-ylmethyl)-1H-indol-3-yl)ethyl]amino]methylpiperidine;
1-cyclohexylmethyl-3-[N-methyl-N-[2-(5-(1,2,4-triazol-1-ylmethyl)-1H-indol-3-yl)ethyl]amino]methylpiperidine;
1-benzyl-2-[2-[N-methyl-N-[2-(5-(1,2,4-triazol-1-ylmethyl)-1H-indol-3-yl)ethyl]amino]ethyl]piperidine;
1-cyclohexylmethyl-2-[2-[N-methyl-N-[2-(5-(1,2,4-triazol-1-ylmethyl)-1H-indol-3-yl)ethyl]amino]ethyl]piperidine;
1-benzyl-3-(R)-[N-methyl-N-[2-(5-(1,2,4-triazol-1-ylmethyl)-1H-indol-3-yl)ethyl]amino]pyrrolidine;
1-benzyl-3-(S)-[N-methyl-N-[2-(5-(1,2,4-triazol-1-ylmethyl)-1H-indol-3-yl)ethyl]amino]pyrrolidine;
1-(4-fluorobenzyl)-3-(R)-[N-methyl-N-[2-(5-(1,2,4-triazol-1-ylmethyl)-1H-indol-3-yl)ethyl]amino]pyrrolidine;
1-(4-fluorobenzyl)-3-(R)-[N-methyl-N-[2-(5-(1,2,4-triazol-4-yl)-1H-indol-3-yl)ethyl]amino]pyrrolidine;
1-benzyl-4-[N-methyl-N-[2-(5-(1,2,4-triazol-4-yl)-1H-indol-3-yl)ethyl]amino]piperidine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises attachment of the $R^1$ moiety to a compound of formula III:

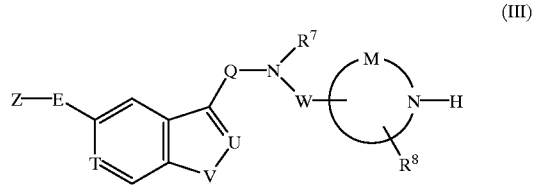

(III)

wherein Z, E, Q, T, U, V, W, M, $R^7$ and $R^8$ are as defined above; by conventional means including N-alkylation.

Attachment of the $R^1$ moiety to the compounds of formula III may conveniently be effected by standard alkylation techniques. One example thereof comprises treatment with a $C_{3-7}$ cycloalkyl($C_{1-6}$)alkyl, aryl($C_{1-6}$)alkyl or heteroaryl ($C_{1-6}$)alkyl halide such as benzyl bromide or 2-bromoethylbenzene, in the presence of a base such as sodium carbonate or potassium carbonate, in a suitable solvent such as isopropanol or 1,2-dimethoxyethane, typically with the addition of a small quantity of sodium iodide.

Alternatively, the $R^1$ moiety may conveniently be attached by reductive alkylation, which may be accomplished in a single step, or as a two-step procedure. The single-step approach suitably comprises treating the required compound of formula III as defined above with the appropriate aldehyde, e.g. benzaldehyde, pyridine carboxaldehyde, furfuraldehyde or thiophene carboxaldehyde, in the presence of a reducing agent such as sodium cyanoborohydride. In a typical two-step procedure, for the preparation of a compound of formula I wherein $R^1$ corresponds to a group of formula —$CH_2R^{11}$, a carboxylic acid derivative of formula $R^{11}$—$CO_2H$ is condensed with the required compound of formula III, suitably in the presence of 1-(3-dimethylaminopropyl)-3-ethylcarbodiimide hydrochloride and 1-hydroxybenzotriazole hydrate, to afford a compound corresponding to formula I wherein $R^1$ represents —$COR^{11}$; the carbonyl group thereof can then be reduced, for example by treatment with diisobutylaluminium hydride, and the required compound of formula I thereby obtained.

The compounds of formula III above wherein T represents CH, U represents C—$R^2$ and V represents N—$R^3$, corresponding to the indole derivatives of formula IE as defined above wherein T represents CH and $R^1$ is hydrogen, may be prepared by a process which comprises reacting a compound of formula IV:

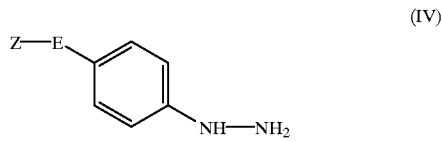

(IV)

wherein Z and E are as defined above; with a compound of formula V, or a carbonyl-protected form thereof:

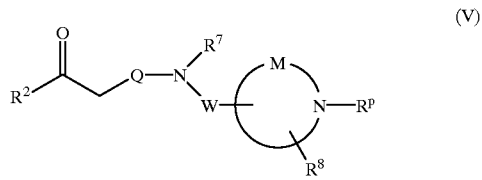

(V)

wherein Q, W, M, $R^2$, $R^7$ and $R^8$ are as defined above, and $R^p$ represents an amino-protecting group; followed, where required, by N-alkylation by standard methods to introduce the moiety $R^3$; with subsequent removal of the amino-protecting group $R^p$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group $R^p$ in the compounds of formula V is suitably a carbamoyl moiety such as tert-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

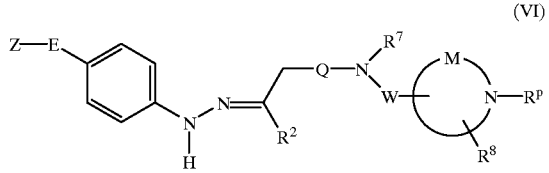

(VI)

wherein Z, E, Q, W, M, $R^2$, $R^7$, $R^8$ and $R^p$ are as defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII:

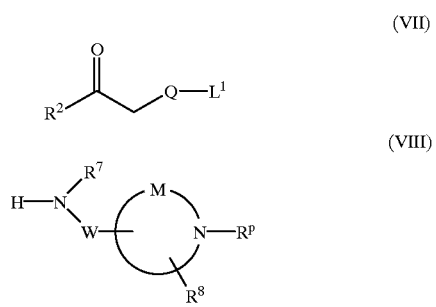

(VII)

(VIII)

wherein Q, W, M, $R^2$, $R^7$, $R^8$ and $R^p$ are as defined above, and $L^1$ represents a suitable leaving group.

The leaving group $L^1$ is suitably a halogen atom, e.g. chlorine or bromine.

Where $L^1$ represents a halogen atom, the reaction between compounds VII and VIII is conveniently effected by stirring the reactants under basic conditions in a suitable solvent, for example sodium carbonate in 1,2-dimethoxyethane, typically in the presence of catalytic sodium iodide.

The compounds according to the invention wherein T represents CH, U represents C—$R^2$ and V represents N—$R^3$—i.e. the indole derivatives of formula IE as defined above wherein T represents CH—may alternatively be prepared by a process which comprises reacting a compound of formula IV as defined above with a compound of formula IX, or a carbonyl-protected form thereof:

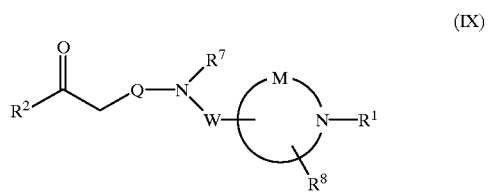

(IX)

wherein Q, W, M, $R^1$, $R^2$, $R^7$ and $R^8$ are as defined above; under conditions analogous to those described above for the reaction between compounds IV and V; followed, where required, by N-alkylation by standard methods to introduce the moiety $R^3$.

As for the compounds of formula V, suitable carbonyl-protected forms of the compounds of formula IX include the dimethyl acetal or ketal derivatives. Where the alkylene chain Q is substituted by a hydroxy group, this group may condense with the carbonyl moiety in compounds V and IX, whereby the carbonyl moiety is protected in the form of a cyclic hemiacetal.

As with that between compounds IV and V, the Fischer reaction between compounds IV and IX may be carried out in a single step, or may proceed via an initial non-cyclising step at a lower temperature to give an intermediate of formula X:

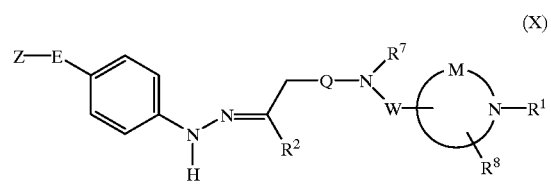

(X)

wherein Z, E, Q, W, M, $R^1$, $R^2$, $R^7$ and $R^8$ are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

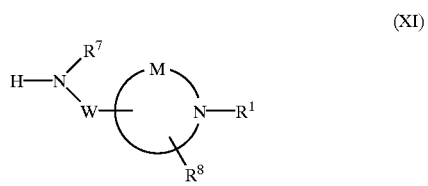

(XI)

wherein W, M, $R^1$, $R^7$ and $R^8$ are as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

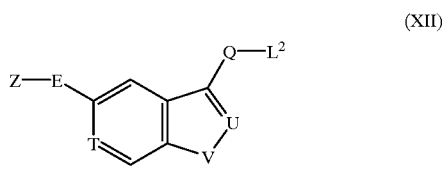

(XII)

wherein Z, E, Q, T, U and V are as defined above, and $L^2$ represents a suitable leaving group; followed by removal of the amino-protecting group $R^p$.

Similarly, the compounds of formula I as defined above may be prepared by a process which comprises reacting a compound of formula XI as defined above with a compound of formula XII as defined above.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compound XII and compound VIII or XI is conveniently carried out in a suitable solvent such as 1,2-dimethoxyethane or isopropyl alcohol, optionally in the presence of a cosolvent such as acetonitrile, typically in the presence of a base such as sodium carbonate or potassium carbonate, and optionally with the addition of a catalytic amount of sodium iodide.

In a representative embodiment, the compounds of formula XII wherein T and U both represent CH, V represents NH, Q represents a propylene chain and $L^2$ represents a mesyloxy or tosyloxy group may be prepared by reacting 3,4-dihydro-2H-pyran with a compound of formula IV as defined above or a salt thereof, under a variant of the Fischer reaction conditions as described above for the reaction between compounds IV and V; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the hydrazine derivative IV or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In an alternative approach, the intermediates of formula XII may be prepared by the procedure described in *Tetrahedron Lett.*, 1994, 35, 6981, or by methods analogous thereto.

In a further procedure, the compounds of formula III above wherein T represents CH, U represents nitrogen and V represents N—$R^3$, corresponding to the indazole derivatives of formula IC as defined above wherein $R^1$ is hydrogen, may be prepared by a process which comprises cyclising a compound of formula XIII:

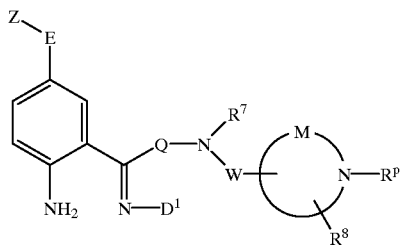

(XIII)

wherein Z, E, Q, W, M, $R^7$, $R^8$ and $R^p$ are as defined above, and $D^1$ represents a readily displaceable group; followed, where required, by N-alkylation by standard methods to introduce the moiety $R^3$; with subsequent removal of the amino-protecting group $R^p$.

Similarly, the compounds of formula I wherein T represents CH, U represents nitrogen and V represents N—$R^3$—i.e. the indazole derivatives of formula IC as defined above—may be prepared by a process which comprises cyclising a compound of formula XIV:

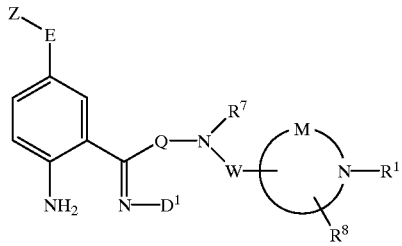

(XIV)

in which Z, E, Q, W, M, $R^1$, $R^7$, $R^8$ and $D^1$ are as defined above; followed, where required, by N-alkylation by standard methods to introduce the moiety $R^3$.

The cyclisation of compounds XIII and XIV is conveniently achieved in a suitable organic solvent at an elevated temperature, for example in a mixture of m-xylene and 2,6-lutidine at a temperature in the region of 140° C.

The readily displaceable group $D^1$ in the compounds of formula XIII and XIV suitably represents a $C_{1-4}$ alkanoyloxy group, preferably acetoxy. Where $D^1$ represents acetoxy, the desired compound of formula XIII or XIV may be conveniently prepared by treating a carbonyl compound of formula XV:

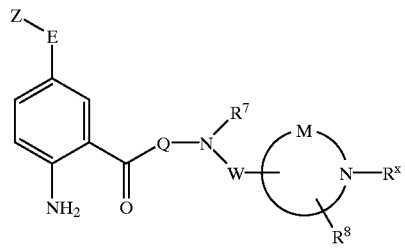

(XV)

wherein Z, E, Q, W, M, $R^7$ and $R^8$ are as defined above, and $R^x$ corresponds to the group $R^1$ as defined above, or $R^x$ represents an amino-protecting group as defined for $R^p$; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XV may conveniently be prepared by ozonolysis of the corresponding indole derivative of formula XVI:

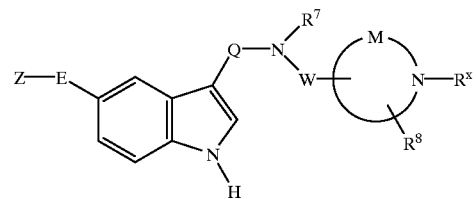

(XVI)

wherein Z, E, Q, W, M, $R^7$, $R^8$ and $R^x$ are as defined above; followed by a reductive work-up, advantageously using dimethylsulphide.

The indole derivatives of formula XVI may be prepared by methods analogous to those described in the accompanying Examples, or by procedures well known from the art.

In a still further procedure, the compounds of formula III above wherein T represents CH, U represents C—$R^2$ and V represents oxygen or sulphur, corresponding to the benzofuran or benzthiophene derivatives of formula IB wherein V is oxygen or sulphur respectively and $R^1$ is hydrogen, may be prepared by a process which comprises cyclising a compound of formula XVII:

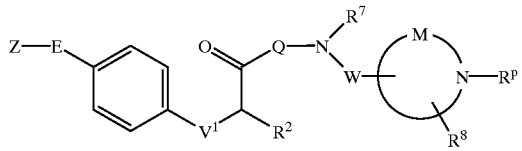

(XVII)

wherein Z, E, Q, W, M, $R^2$, $R^7$, $R^8$ and $R^p$ are as defined above, and VI represents oxygen or sulphur; followed by removal of the amino-protecting group $R^p$.

Similarly, the compounds of formula I wherein T represents CH, U represents C—$R^2$ and V represents oxygen or sulphur—i.e. the benzofuran or benzthiophene derivatives of formula IB above—may be prepared by a process which comprises cyclising a compound of formula XVIII:

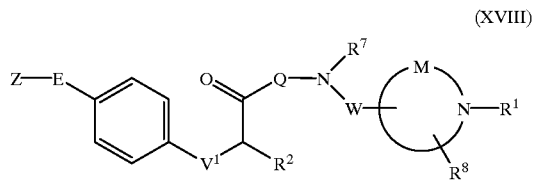
(XVIII)

wherein Z, E, Q, W, M, $R^1$, $R^2$, $R^7$, $R^8$ and $V^1$ are as defined above.

The cyclisation of compounds XVII and XVIII is conveniently effected by using polyphosphoric acid or a polyphosphate ester, advantageously at an elevated temperature.

The compounds of formula XVII and XVIII may be prepared by reacting a compound of formula XIX with a compound of formula XX:

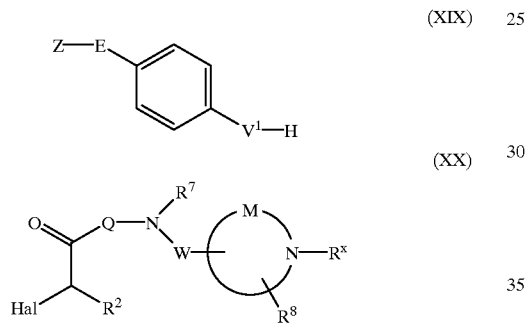
(XIX)

(XX)

wherein Z, E, Q, W, M, $R^2$, $R^7$, $R^8$, $R^x$ and $V^1$ are as defined above, and Hal represents a halogen atom.

The reaction is conveniently effected in the presence of a base such as sodium hydroxide.

The hydroxy and mercapto derivatives of formula XIX may be prepared by a variety of methods which will be readily apparent to those skilled in the art. One such method is described in EP-A-0497512.

In a yet further procedure, the compounds of formula III above may be prepared by a process which comprises reducing a compound of formula XXI:

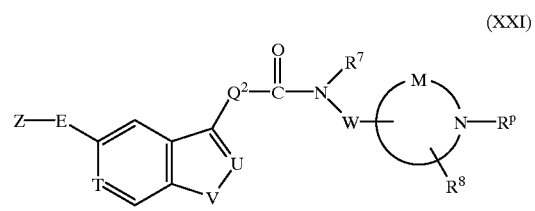
(XXI)

wherein Z, E, T, U, V, W, M, $R^7$, $R^8$ and $R^p$ are as defined above, and —$Q^2$—$CH_2$— corresponds to the moiety Q as defined above; with subsequent removal of the amino-protecting group $R^p$.

Similarly, the compounds according to the invention may be prepared by a process which comprises reducing a compound of formula XXII:

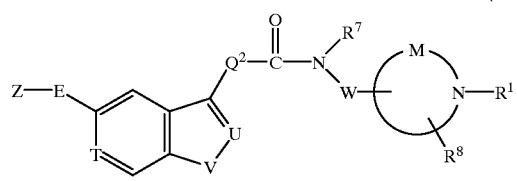
(XXII)

wherein Z, E, T, U, V, W, M, $R^1$, $R^7$, $R^8$ and $Q^2$ are as defined above.

The reduction of compounds XXI and XXII is conveniently effected by treating the appropriate compound with a reducing agent such as lithium aluminium hydride in an appropriate solvent, e.g. diethyl ether or tetrahydrofuran, or mixtures thereof.

The compounds of formulae XXI and XXII above may suitably be prepared by reacting a compound of formula XXIII with the appropriate compound of formula XXIV:

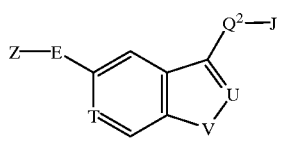
(XXIII)

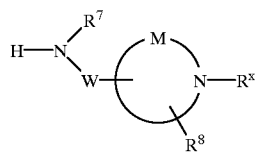
(XXIV)

wherein Z, E, T, U, V, W, M, $R^7$, $R^8$, $R^x$ and $Q^2$ are as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XXIII above wherein J is an acid chloride moiety may be prepared by treating the corresponding carboxylic acid derivative with thionyl chloride in toluene. Similarly, the intermediates of formula XXIII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula XXIV.

In another procedure, the compounds of formula III above may be prepared by a process which comprises reacting a compound of formula XXV with a compound of formula XXVI:

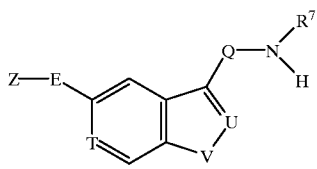
(XXV)

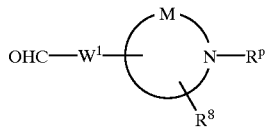
(XXVI)

wherein Z, E, Q, T, U, V, M, $R^7$, $R^8$ and $R^P$ are as defined above, and —$CH_2$—$W^1$— corresponds to the moiety W as defined above; in the presence of a reducing agent; with subsequent removal of the protecting group $R^P$.

Similarly, the compounds according to the invention may be prepared by a process which comprises reacting a compound of formula XXV as defined above with a compound of formula XXVII:

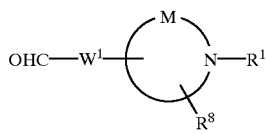
(XXVII)

wherein M, $R^1$, $R^8$ and $W^1$ are as defined above; in the presence of a reducing agent.

In an additional procedure, the compounds of formula III above wherein W represents a chemical bond may be prepared by reacting a compound of formula XXV as defined above with a compound of formula XXVIII:

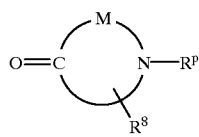
(XXVIII)

wherein M, $R^8$ and $R^P$ are as defined above, in the presence of a reducing agent; with subsequent removal of the protecting group $R^P$.

Similarly, the compounds according to the invention may be prepared by a process which comprises reacting a compound of formula XXV as defined above with a compound of formula XXIX:

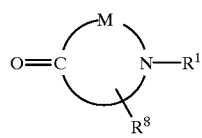
(XXIX)

wherein M, $R^1$ and $R^8$ are as defined above; in the presence of a reducing agent.

A suitable reducing agent for use in the reaction between compound XXV and the appropriate compound of formula XXVI, XXVII, XXVIII or XXIX is sodium cyanoborohydride, in which case the reaction is conveniently carried out in a mixture of methanol and acetic acid.

The compounds of formula XXV may suitably be prepared by reacting a compound of formula XII as defined above with a compound of formula XXX:

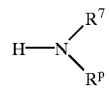
(XXX)

wherein $R^7$ and $R^P$ are as defined above, typically under conditions analogous to those as described above for the reaction between compound XII and compound VIII or XI; with subsequent removal of the protecting group $R^P$.

In relation to compound XXX above, the protecting group $R^P$ is suitably benzyl, which can conveniently be removed as required by transfer hydrogenation using a hydrogenation catalyst such as palladium on charcoal in the presence of a hydrogen donor such as ammonium formate, or alternatively by conventional catalytic hydrogenation.

The hydrazine derivatives of formula IV above may be prepared by methods analogous to those described in EP-A-0438230, EP-A-0497512, EP-A-0548813 and WO-A-91/18897.

Where they are not commercially available, the starting materials of formula VII, VIII, XI, XX, XXIII, XXIV and XXVI to XXX may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein $R^1$ is benzyl initially obtained may be converted by catalytic hydrogenation to the corresponding compound of formula III, which in turn may be converted into a further compound of formula I using standard N-alkylation techniques as described above. Furthermore, a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile. Similarly, a compound of formula I wherein $R^7$ is hydrogen initially obtained may also be alkylated, typically by treatment with the appropriate aldehyde, e.g. formaldehyde, in the presence of a reducing agent such as sodium cyanoborohydride, to afford the corresponding compound of formula I wherein $R^7$ represents $C_{1-6}$ alkyl.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-$HT_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-$HT_{1D\alpha}$/5-$HT_{1D\beta}$ Radioligand Binding

Chinese hamster ovary (CHO) clonal cell lines expressing the human 5-$HT_{1D\alpha}$ and 5-$HT_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharmacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

5-$HT_{1D\alpha}$/5-$HT_{1D\beta}$ GTPγS Binding

Studies were performed essentially as described in *Br. J. Pharmacol.*, 1993, 109, 1120. CHO clonal cell lines expressing the human cloned 5-HT$_{1D\alpha}$ and 5-HT$_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40 μg protein/ml for the 5-HT$_{1D\alpha}$ receptor transfected cells and 40–50 μg protein/ml for the 5-HT$_{1D\beta}$ receptor transfected cells. The membrane suspension was then incubated, in a volume of 1 ml, with GDP (100 μM for 5-HT$_{1D\alpha}$ receptor transfected cells, 30 μM for the 5-HT$_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

EXAMPLE 1

N-(1-Benzylazetidin-3-ylmethyl)-N-[2-(5-(1,2,4-triazol-1-ylmethyl)-1H-indol-3-yl)ethyl]-N-ethylamine Hydrogen Oxalate 1. N-Benzyl-N-ethyl-N-[2-[5-(1,2,4-triazol-1-ylmethyl)-1H-indol-3-yl]ethyl]amine Hydrogen Oxalate A stirred, cooled (−5° C.) solution of 2-[5-(1,2,4-triazol-1-ylmethyl)-1H-indol-3-yl]ethanol (1.20 g, 4.96 mmol, *Tet. Letts.* 1994, 35, 6981–6984) in anhydrous tetrahydrofuran (100 ml) was treated with triethylamine (0.83 ml, 5.95 mmol) and methanesulphonyl chloride (0.47 ml, 5.95 mmol). After stirring at −5° C. for 30 minutes the mixture was filtered and the solids washed through with tetrahydrofuran (25 ml). The mesylate solution was treated with potassium carbonate (0.82 g, 5.95 mmol), sodium iodide (0.89 g, 5.95 mmol), N-ethylbenzylamine (3.6 ml, 24.8 mmol) and water (3 ml). The reaction mixture was stirred whilst heating at reflux for 4 days. The mixture was evaporated then the residue partitioned between dichloromethane (50 ml) and water (20 ml). The organic layer was collected, then extracted with 5M hydrochloric acid (2×30 ml). The aqueous extracts were combined, washed with ethyl acetate (2×30 ml), basified to pH=12 with 40% aqueous sodium hydroxide solution then extracted with dichloromethane (3×30 ml). The combined organic extracts were dried (potassium carbonate) then evaporated to give the crude product which was purified using column chromatography on silica, eluting with dichloromethane/methanol/ammonia (19:1:0.5) to give the title product free base as a pale yellow gum (1.10 g, 62%). The hydrogen oxalate salt had mp 153–156° C. MS, ES$^+$, m/z=360 for (M+H)$^+$; δ (360 MHz, d$_6$-DMSO) 1.26 (3H, t, J=7 Hz), 3.00–3.20 (6H, m), 4.31 (2H, s), 5.41 (2H, s), 7.05 (1H, d, J=8 Hz), 7.23 (1H, d, J=2 Hz), 7.33 (1H, d, J=8 Hz), 7.43–7.47 (4H, m), 7.54–7.57 (2H, m), 7.95 (1H, s), 8.60 (1H, s), 11.02 (1H, s). (Found: C, 61.94; H, 5.77; N, 14.25. C$_{22}$H$_{25}$N$_5$. 1.35C$_2$H$_2$O$_4$ requires C, 61.68; H, 5.80; N, 14.56%).

2. N-Ethyl-N-[2-[5-(1,2,4-triazol-1-ylmethyl)-1H-indol-3-yl]ethyl]amine

A solution of the foregoing benzylamine (1.03 g, 2.87 mmol) in methanol (20 ml) was treated with ammonium formate (0.9 g, 14.3 mmol), formic acid (90%, 1 ml) and 10% palladium on carbon (0.45 g). The reaction mixture was stirred under a nitrogen atmosphere whilst heating at reflux for 3 hours. The mixture was filtered, evaporated to leave ~5 ml of methanol, diluted with dichloromethane (40 ml) then washed with saturated aqueous sodium carbonate (15 ml). The organic layer was separated and the aqueous re-extracted with dichloromethane (3×40 ml). The combined organics were dried (potassium carbonate) then evaporated to give a pale yellow gum which solidified on standing (0.734 g, 95%), mp 106–107° C. δ (250 MHz, d$_6$-DMSO) 0.99 (3H, t, J=7 Hz), 2.55 (2H, q, J=7 Hz), 2.77 (4H, s), 5.43 (2H, s), 7.03 (1H, dd, J$_1$=2, J$_2$=8 Hz), 7.15 (1H, d, J=2 Hz), 7.30 (1H, d, J=8 Hz), 7.51 (1H, s), 7.94 (1H, s), 8.60 (1H, s), 10.85 (1H, s); MS, ES$^+$, m/z=270 for (M+H)$^+$.

3. 1-t-Butyloxycarbonyl-3-hydroxyazetidine

1-Diphenylmethyl-3-hydroxyazetidine hydrochloride (5.5 g, 19.9 mmol; *J. Org. Chem.* 1972, 37, 3953), 20% palladium hydroxide on carbon (0.7 g) and methanol (70 ml) were hydrogenated at 45 psi for 2 hours. The mixture was filtered then evaporated to give 3-hydroxyazetidine hydrochloride (2.2 g). This amine was dissolved in water (40 ml) then treated with sodium hydroxide (1.75 g, 44 mmol), dioxan (80 ml) and di-t-butyldicarbonate (4.79 g, 22 mmol). The reaction mixture was stirred at room temperature for 18 hours then the dioxan was evaporated. The aqueous was extracted with dichloromethane (2×50 ml), then the combined organics were dried (sodium sulphate) and evaporated to give the title compound (3.1 g, 90%). δ (360 MHz, d$_6$-DMSO) 1.37 (9H, s), 3.58 (2H, dd, J$_1$=4, J$_2$=9 Hz), 3.99 (2H, dd, J$_1$=7, J$_2$=9 Hz), 4.30–4.45 (1H, m), 5.62 (1H, d, J=6 Hz).

4. 1-t-Butyloxycarbonyl-3-cyanoazetidine

A stirred, cooled (5° C.) solution of the foregoing alcohol (25 g, 0.144 mol) in dichloromethane (600 ml) was treated with triethylamine (32 ml, 0.23 mol) followed by dropwise addition of methanesulphonyl chloride (16.7 ml, 0.216 mol). After addition the cooling bath was removed and the reaction mixture stirred at room temperature for 2 hours. The solution was washed with water (2×200 ml), dried (sodium sulphate) and evaporated to give the mesylate as a gum (36 g). This mesylate in toluene (800 ml) was treated with tetrabutylammonium cyanide (55 g, 0.20 mol) and the reaction mixture was stirred under a nitrogen atmosphere, whilst heating at reflux, for 18 hours. Water (200 ml) was added to the cooled reaction mixture and the organic layer was separated. The aqueous was extracted with ethyl acetate (4×200 ml) then the combined organics were evaporated. The crude product was purified using column chromatography eluting with dichloromethane→10% methanol in dichloromethane. The title compound was obtained (14.7 g, 56%) as a gum. δ (360 MHz, d$_6$-DMSO) 1.39 (9H, s), 3.65–3.78 (1H, m), 3.99 (2H, dd, J$_1$=6, J$_2$=9 Hz), 4.12 (2H, dd, J$_1$=J$_2$=9 Hz).

5. 1-t-Butyloxycarbonyl-3-azetidinecarboxaldehyde

Diisobutylaluminium hydride (33 ml of a 1M dichloromethane solution, 33 mmol) was added dropwise to a stirred, cooled (0° C.) solution of the foregoing nitrile (3.0 g, 16.5 mmol) in dichloromethane (30 ml) under a nitrogen atmosphere. The cooling bath was removed and the reaction mixture was stirred at room temperature for 1 hour 40 minutes. The mixture was cooled to 0° C. and quenched with saturated aqueous ammonium chloride (20 ml). The mixture was warmed to room temperature and 2M hydrochloric acid was added to break up the gelatinous mixture. The aqueous was extracted with dichloromethane (5×50 ml), the combined extracts dried (sodium sulphate) then evaporated to give the required aldehyde as a gum (1.95 g, 64%). δ (250 MHz, CDCl$_3$) 1.44 (9H, s), 3.30–3.45 (1H, m), 4.08–4.17 (4H, m), 9.85 (1H, d, J=3 Hz).

6. N-(1-t-Butyloxycarbonylazetidin-3-ylmethyl)-N-[2-(5-(1,2,4-triazol-1-ylmethyl)-1H-indol-3-yl)ethyl]-N-ethylamine Hydrogen Oxalate A solution of N-ethyl-N-[2-[5-(1,2,4-triazol-1-ylmethyl)-1H-indol-3-yl]ethyl]amine (200 mg, 0.743 mmol) in methanol (15 ml) was treated with a solution of 1-t-butyloxycarbonyl-3-azetidinecarboxaldehyde (206 mg, 1.11 mmol) in methanol (5 ml) followed by glacial acetic acid (0.21 ml, 3.72 mmol). After 2 minutes sodium cyanoborohydride (70 mg, 1.11 mmol) was added and the reaction mxiture was stirred at room temperature for 20 hours. The reaction was basified to pH=10 with saturated aqueous potassium carbonate, the methanol was evaporated and the residue extracted with dichloromethane (3×30 ml). The combined organics were washed with water (30 ml), dried (potassium carbonate) and evaporated to give a gum (400 mg) which was purified using column chromatography on silica, eluting with dichloromethane/methanol/ammonia (10:1:0.1) to give the title compound free base as a viscous, colourless gum (180 mg, 55%). The hydrogen oxalate salt had mp 75–79° C. MS, ES$^+$, m/z=439 for (M+H)$^+$; δ (360 MHz, d$_6$-DMSO) 1.23 (3H, t, J=7 Hz), 1.39 (9H, s), 2.98–3.10 (3H, m), 3.17 (2H, q, J=7 Hz), 3.20–3.26 (2H, m), 3.44 (2H, d, J=6 Hz), 3.80–4.00 (4H, m), 5.46 (2H, s), 7.09 (1H, d, J=8 Hz), 7.30 (1H, s), 7.36 (1H, d, J=8 Hz), 7.59 (1H, s), 7.95 (1H, s), 8.60 (1H, s), 11.06 (1H, s). (Found: C, 54.72; H, 6.40; N, 13.67. C$_{24}$H$_{34}$N$_6$O$_2$. 2C$_2$H$_2$O$_4$ requires C, 54.36; H, 6.19; N, 13.58%).

7. N-(1-Benzylazetidin-3-ylmethyl)-N-[2-(5-(1,2,4-triazol-1-ylmethyl)-1H-indol-3-yl)ethyl]-N-ethylamine Hydrogen Oxalate A solution of N-(1-t-butyloxycarbonylazetidin-3-ylmethyl)-N-[2-(5-(1,2,4-triazol-1-ylmethyl)-1H-indol-3-yl)ethyl]-N-ethylamine (155 mg, 0.353 mmol) in dichloromethane (10 ml) was treated with trifluoroacetic acid (0.27 ml, 3.53 mmol) and stirred at room temperature for 20 hours. The reaction mixture was evaporated and excess trifluoroacetic acid removed by addition of toluene (3×20 ml) followed by evaporation. N-(Azetidin-3-ylmethyl)-N-[2-(5-(1,2,4-triazol-1-ylmethyl)-1H-indol-3-yl)ethyl]-N-ethylamine bis-trifluoroacetate was obtained as a yellow gum (197 mg). This amine was dissolved in methanol (20 ml) and the pH adjusted to 10 with a 30% sodium methoxide solution in methanol. Benzaldehyde (0.11 ml, 0.70 mmol) was added followed by glacial acetic acid (0.1 ml, 1.75 mmol). After two minutes sodium cyanoborohydride (44 mg, 0.70 mmol) was added and the reaction mixture was stirred at room temperature for 20 hours. The reaction mixture was quenched with saturated aqueous potassium carbonate (10 ml), the methanol was evaporated, and the aqueous extracted with dichloromethane (3×20 ml). The combined organics were extracted with 5M hydrochloric acid (2×25 ml). The combined aqueous extracts were washed with ethyl acetate (25 ml), basified to pH=12 with 40% aqueous sodium hydroxide then extracted with dichloromethane (3×30 ml). The combined organic extracts were dried (potassium carbonate) then evaporated to give a yellow gum (190 mg) which was purified using column chromatography on silica, eluting with dichloromethane/methanol/ammonia (19:1:0.1→9:1:0.1) to give the title compound free base as a colourless gum (88 mg, 59%). The hydrogen oxalate salt had mp 105–110° C. (foamed). MS, ES$^+$, m/z=429 for (M+H)$^+$; δ (250 MHz, d$_6$-DMSO) 1.18 (3H, t, J=7 Hz), 3.00–3.20 (7H, m), 3.34–3.38 (2H, m), 3.75–3.85 (2H, m), 3.95–4.05 (2H, m), 4.27 (2H, s), 5.44 (2H, s), 7.07 (1H, d, J=8 Hz), 7.27 (1H, s), 7.34 (1H, d, J=8 Hz), 7.43 (5H, s), 7.58 (1H, s), 7.95 (1H, s), 8.60 (1H, s), 11.05 (1H, s). (Found: C, 57.03; H, 5.93; N, 12.48. C$_{26}$H$_{32}$N$_6$. 2.5 C$_2$H$_2$O$_4$ requires C, 56.96; H, 5.71; N, 12.86%).

EXAMPLE 2

N-(1-Cyclohexylmethylazetidin-3-ylmethyl)-N-[2-(5-(1,2,4-triazol-1-ylmethyl)-1H-indol-3-yl)ethyl]-N-methylamine Hydrogen Oxalate 1. N-Methyl-N-[2-[5-(1,2,4-triazol-1-ylmethyl)-1H-indol-3-yl]ethyl]amine The title compound was prepared using the procedures described in Example 1, steps 1 and 2, using N-methylbenzylamine. mp 139–141° C.; δ (360 MHz, d$_6$-DMSO) 2.45 (3H, s), 2.90–2.98 (4H, m), 5.43 (2H, s), 7.04 (1H, dd, J$_1$=2, J$_2$=8 Hz), 7.21 (1H, d, J=2 Hz), 7.32 (1H, d, J=8 Hz), 7.57 (1H, s), 7.94 (1H, s), 8.49 (1H, s), 8.62 (1H, s), 11.00 (1H, s); MS, ES$^+$, m/z=256 for (M+H)$^+$.

2. N-(1-Cyclohexylmethylazetidin-3-ylmethyl)-N-[2-(5-(1,2,4-triazol-1-ylmethyl)-1H-indol-3-yl)ethyl]-N-methylamine Hydrogen Oxalate The title compound free base was prepared using the procedures described in Example 1, replacing benzaldehyde with cyclohexane carboxaldehyde in the final step. The hydrogen oxalate salt had mp>135° C. MS, ES$^+$, m/z=421 for (M+H)$^+$.

The following compounds were prepared using the procedures described in Examples 1 and 2.

EXAMPLE 3

N-(1-Benzylazetidin-3-ylmethyl)-N-[2-(5-(1,2,4-triazol-1-ylmethyl)-1H-indol-3-yl)ethyl]-N-methylamine Hydrogen Oxalate mp>130° C. (dec). MS, ES$^+$, m/z=415 for (M+H)$^+$; (Found: C, 58.22; H, 5.91; N, 13.52. C$_{25}$H$_{30}$N$_6$. 2.2 C$_2$H$_2$O$_4$ requires C, 58.10; H, 5.71; N, 13.92%).

EXAMPLE 4

N-[1-(2-Chlorobenzyl)azetidin-3-ylmethyl]-N-[2-(5-(1,2,4-triazol-1-ylmethyl)-1H-indol-3-yl)ethyl]-N-methylamine Hydrogen Oxalate mp>134° C. (dec). MS, ES$^+$, m/z=450 for (M+H)$^+$.

EXAMPLE 5

N-[1-(4-Fluorobenzyl)azetidin-3-ylmethyl]-N-[2-(5-(1,2,4-triazol-1-ylmethyl)-1H-indol-3-yl)ethyl]-N-methylamine Hydrogen Oxalate mp>140° C. (dec). MS, ES$^+$, m/z=433 for (M+H)$^+$.

EXAMPLE 6

N-[1-(2-Trifluoromethylbenzyl)azetidin-3-ylmethyl]-N-[2-(5-(1,2,4-triazol-1-ylmethyl)-1H-indol-3-yl)ethyl]-N-methylamine Hydrogen Oxalate mp 140–144° C. (dec). MS, ES$^+$, m/z=483 for (M+H)$^+$. (Found: C, 53.69; H, 5.03; N, 12.34. C$_{26}$H$_{29}$F$_3$N$_6$. 2.1 C$_2$H$_2$O$_4$ requires C, 54.01; H, 4.98; N, 12.51%).

EXAMPLE 7

N-[1-(2-Chloro-6-fluorobenzyl)azetidin-3-ylmethyl]-N-[2-(5-(1,2,4-triazol-1-ylmethyl)-1H-indol-3-yl)ethyl]-N-methylamine Hydrogen Oxalate mp>120° C. (dec). MS, ES$^+$, m/z=467 for (M+H)$^+$. (Found: C, 52.18; H, 5.09; N, 12.31. $C_{25}H_{28}ClFN_6 \cdot 2C_2H_2O_4 \cdot H_2O$ requires C, 52.37; H, 5.15; N, 12.64%).

EXAMPLE 8

N-(1-Benzyl-3-hydroxyazetidin-3-ylmethyl)-N-[2-(5-(1,2,4-triazol-1-ylmethyl)-1H-indol-3-yl)ethyl]-N-methylamine Hydrogen Oxalate 1. 1-Diphenylmethyl-3-azetidinone A solution of 1-diphenylmethyl-3-hydroxyazetidine (3.3 g, 14 mmol; J. Org. Chem. 1972, 37, 3953) in dimethyl sulphoxide (20 ml) was treated with triethylamine (19.2 ml), cooled to 15° C. and treated with sulphur trioxide pyridine (13.8 g) in dimethyl sulphoxide (30 ml), keeping the temperature below 20° C. The solution was stirred under an atmosphere of nitrogen at 15° C. for 45 minutes then at room temperature for 45 minutes. The solution was poured into ice water and extracted twice with ethyl acetate. The organic layer was collected, washed twice with water, dried (sodium sulphate), evaporated to dryness and the crude product purified using a plug of silica by eluting with dichloromethane to afford the ketone as a gum (2.9 g, 89%), δ (360 MHz, CDCl$_3$) 4.00 (4H, s), 4.59 (1H, s), 7.12–7.49 (10H, m).

2. 1-Oxa-5-aza-5-(diphenylmethyl)spiro[2.3]hexane

A mixture of trimethylsulphoxonium iodide (465 mg, 2.1 mmol), sodium hydride (93 mg of a 55% oil dispersion, 2.1 mmol) and dimethylformamide (10 ml) was cooled to 4° C. and treated with dimethyl sulphoxide (150 μl, 2.1 mmol). After stirring at 4° C. for 20 minutes a solution of 1-diphenylmethyl-3-azetidinone (500 mg, 2.1 mmol) in dimethylformamide (5 ml) was added dropwise. The reaction mixture was stirred for 30 minutes at 4° C. then quenched with water. The aqueous was extracted twice with ethyl acetate. The combined organics were washed with water (3 times), dried (sodium sulphate) then evaporated to dryness. The residue was filtered through a plug of silica eluting with dichloromethane to afford the title epoxide as a gum (260 mg, 52%), δ (250 MHz, d$_6$-DMSO) 2.73 (2H, s), 3.26 (2H, d, J=10 Hz), 3.46 (2H, d, J=10 Hz), 4.82 (1H, s), 7.14–7.51 (10 H, m).

3. N-(1-Diphenylmethyl-3-hydroxyazetidin-3-ylmethyl)-N-[2-(5-(1,2,4-triazol-1-ylmethyl)-1H-indol-3-yl)ethyl]-N-methylamine The foregoing epoxide (260 mg) and N-methyl-N-[2-[5-(1,2,4-triazol-1-ylmethyl)-1H-indol-3-yl]ethyl]amine (250 mg, 1 mmol) were stirred at room temperature in ethanol (20 ml) for 24 hours. The ethanol was evaporated and the residue partitioned between dichloromethane and water. The aqueous was re-extracted with dichloromethane. The combined organics were dried (sodium sulphate) and the solvent evaporated. The residue was purified by column chromatography on silica using dichloromethane/methanol (10:1) to afford the title compound as a gum (140 mg, 27%), δ (250 MHz, d$_6$-DMSO) 2.34 (3H, s), 2.68–2.85 (8H, m), 3.16 (2H, d, J=8 Hz), 4.41 (1H, s), 4.99 (1H, br s), 5.41 (2H, s), 7.00–7.52 (14H, m), 7.93 (1H, s), 8.60 (1H, s), 10.85 (1H, s).

4. N-(1-Benzyl-3-hydroxyazetidin-3-ylmethyl)-N-[2-(5-(1,2,4-triazol-1-ylmethyl)-1H-indol-3-yl)ethyl]-N-methylamine Hydrogen Oxalate The foregoing amine (140 mg, 0.27 mmol), 20% palladium hydroxide on carbon (140 mg), glacial acetic acid (33 μl, 0.56 mmol) and ethanol (20 ml) were hydrogenated at 50 psi for 24 hours at room temperautre. The mixture was filtered and the solvent evaporated. The crude product was re-dissolved in methanol (10 ml), treated with benzaldehyde (30 μl, 0.3 mmol) then sodium cyanoborohydride (19 mg, 0.3 mmol) and stirred at room temperature for 24 hours. 10% potassium carbonate solution (5ml) was added, the solvent evaporated and the residue partitioned between water and dichloromethane. The organic layer was separated and the aqueous re-extracted with dichloromethane. The combined organics were dried (sodium sulphate), evaporated and the residue purified by column chromatography on silica using dichloromethane/methanol/ammonia (10:1:0.1). The title compound free base was obtained as a gum (35 mg, 30%). The hydrogen oxalate salt had mp>100° C. (sint.); δ (500 MHz, d$_6$-DMSO) 2.73 (3H, s), 3.00–3.05 (2H, m), 3.12–3.23 (2H, m), 3.31 (2H, s), 3.57 (2H, d, J=8 Hz), 3.82 (2H, d, J=8 Hz), 4.01 (2H, s), 5.43 (2H, s), 7.05 (1H, dd, J$_1$=1.25, J$_2$=8 Hz), 7.22 (1H, d, J=2 Hz), 7.30–7.42 (6H, m), 7.57 (1H, s), 7.94 (1H, s), 8.06 (1H, s), 10.98 (1H, s). MS, ES$^+$, m/z=431 for (M+H)$^+$. (Found: C, 54.31; H, 5.41; N, 12.78. $C_{25}H_{30}N_6O \cdot 2.5C_2H_2O_4 \cdot 0.5 H_2O$ requires C, 54.21; H, 5.46; N, 12.64%).

EXAMPLE 9

N-(1-Benzyl-3(RS)-pyrrolidin-3-ylmethyl)-N-[2-(5-(1,2,4-triazol-1-ylmethyl)-1H-indol-3-yl)ethyl]-N-methylamine Hydrogen Oxalate 1. N-(1-t-Butyloxycarbonyl-3(RS)-pyrrolidin-3-ylmethyl)-N-[2-(5-(1,2,4-triazol-1-ylmethyl)-1H-indol-3-yl)ethyl]-N-methylamine A solution of 3(RS)-pyrrolidin-3-ylmethanol (3 g, 29.8 mmol) in dioxan (50 ml) was treated with a solution of sodium hydroxide (1.2 g, 29.8 mmol) in water (20 ml) and di-t-butyldicarbonate (6.51 g, 29.8 mmol), then stirred at room temperature for 24 hours. The solvent was evaporated and the residue partitioned between water (25 ml) and dichloromethane (50 ml). The organic layer was separated and the aqueous re-extracted with dichloromethane (3×50 ml). The combined organics were dried (sodium sulphate) and the solvent evaporated. The crude product was purified by column chromatography on silica using dichloromethane/methanol (19:1) to give the product as a gum (2.3 g, 38%). This alcohol (1.3 g, 6.47 mmol) in dichloromethane (50 ml) was treated with triethylamine (1.08 ml, 7.76 mmol) and methanesulphonyl chloride (601 μl, 7.76 mmol), then the reaction mixture was stirred at room temperature for 2 hours. Water (20 ml) was added, the organic layer separated and the aqueous re-extracted with dichloromethane (2×50 ml). The combined organics were dried (potassium carbonate) then evaporated to give the mesylate as a gum (1.8 g, 99%). This mesylate (219 mg, 0.78 mmol), N-methyl-N-[2-[5-(1,2,4-triazol-1-ylmethyl)-1H-indol-3-yl]ethyl]amine (200 mg, 0.78 mmol) and potassium carbonate (108 mg, 0.78 mmol) were heated at reflux, with stirring, in propan-2-ol (20 ml) for 18 hours. The solvent was evaporated and the residue partitioned between water (20 ml) and dichloromethane (50 ml). The organic layer was separated and the aqueous re-extracted with dichloromethane (50 ml). The combined organics were dried (potassium carbonate), evaporated and the crude product purified by column chromatography on silica using dichloromethane/methanol (9:1). The title compound was obtained as a gum (106 mg, 31%). $R_f$=0.38 in dichloromethane/methanol/ammonia (9:1:0.1) on silica. MS, ES$^+$, m/z=439 for (M+H)$^+$.

2. N-(1-Benzyl-3(RS)-pyrrolidin-3-ylmethyl)-N-[2-(5-(1,2,4-triazol-1-ylmethyl)-1H-indol-3-yl)ethyl]-N-methylamine Hydrogen Oxalate The foregoing pyrrolidine (106 mg, 0.24 mmol) and trifluoroacetic acid (5 ml) were stirred in dichloromethane (15 ml) for 18 hours. The solvent was evaporated, and the residue azeotroped with toluene to afford N-(3(RS)-pyrrolidin-3-ylmethyl)-N-[2-(5-(1,2,4-triazol-1-ylmethyl)-1H-indol-3-yl)ethyl]-N-methylamine bis-trifluoroacetate as a gum. This gum was dissolved in methanol (10 ml), treated with sodium methoxide to pH=7 then re-acidified to pH=5 with glacial acetic acid. Benzaldehyde (24.6 µl, 0.24 mmol) was added followed by sodium cyanoborohydride (15 mg, 0.24 mmol). The reaction mixture was stirred at room temperature for 18 hours then treated with 10% potassium carbonate solution (30 ml). The methanol was evaporated and the aqueous extracted with dichloromethane (4×50 ml). The combined organics were dried (potassium carbonate) then evaporated to give the crude product which was purified by column chromatography on silica using dichloromethane/methanol/ammonia (19:1:0.2) to afford the title compound free base as a gum (80 mg, 77%). The hydrogen oxalate salt had mp>130° C. (dec); δ (360 MHz, d$_6$-DMSO) 1.60–1.75 (1H, m), 2.05–2.20 (1H, m), 2.64 (3H, s), 2.60–2.70 (1H, m), 2.80–2.88 (1H, m), 2.92–3.16 (8H, m), 3.20–3.30 (1H, m), 4.15 (2H, s), 5.44 (2H, s), 7.06 (1H, dd, J$_1$=1.5, J$_2$=8 Hz), 7.21 (1H, s), 7.33 (1H, d, J=8 Hz), 7.35–7.50 (5H, m), 7.56 (1H, s), 7.94 (1H, s), 8.80 (1H, s), 10.98 (1H, s). MS, ES$^+$, m/z=429 for (M+H)$^+$. (Found: C, 58.68; H, 6.14; N, 13.28. $C_{26}H_{32}N_6$. $2C_2H_2O_4$. $0.5H_2O$ requires C, 58.34; H, 6.04; N, 13.61%).

EXAMPLE 10

N-(1-Benzyl-3(RS)-piperidin-3-ylmethyl)-N-[2-(5-(1,2,4-triazol-1-ylmethyl)-1H-indol-3-yl)ethyl]-N-methylamine Hydrogen Oxalate The title compound was prepared from 3-piperidinemethanol using the procedures described in Example 9. The hydrogen oxalate salt had mp>100° C. (dec.); δ (360 MHz, d$_6$-DMSO) 1.00–1.12 (1H, m), 1.60–1.80 (3H, m), 2.15–2.30 (1H, m), 2.30–2.40 (1H, m), 2.50–2.60 (1H, m), 2.68 (3H, s), 2.80–2.90 (2H, m), 2.95–3.30 (6H, m), 3.94 (1H, d, J=7 Hz), 3.97 (1H, d, J=7 Hz), 5.45 (2H, s), 7.07 (1H, d, J=8 Hz), 7.24 (1H, s), 7.30–7.42 (6H, m), 7.59 (1H, s), 7.95 (1H, s), 8.63 (1H, s), 11.01 (1H, s). MS, ES$^+$, m/z=443 for (M+H)$^+$. (Found: C, 58.81; H, 6.37; N, 13.09. $C_{27}H_{34}N_6$. $2C_2H_2O_4$. $0.5H_2O$ requires C, 58.94; H, 6.22; N, 13.30%).

EXAMPLE 11

N-(1-Cyclohexylmethyl)-3(RS)-piperidin-3-ylmethyl)-N-[2-(5-(1,2,4-triazol-1-ylmethyl)-1H-indol-3-yl)ethyl]-N-methylamine Hydrogen Oxalate The title compound was prepared from 3-piperidinemethanol using the procedures described in Example 9, replacing benzaldehyde with cyclohexane carboxaldehyde in the final step. The hydrogen oxalate salt had mp>100° C. (dec.); δ (360 MHz, d$_6$-DMSO) 0.80–1.00 (2H, m), 1.10–1.40 (4H, m), 1.60–1.90 (9H, m), 2.20–2.35 (1H, m), 2.45–2.60 (1H, m), 2.68 (3H, s), 2.60–2.90 (5H, m), 2.95–3.10 (4H, m), 3.25–3.45 (2H, m), 5.45 (2H, s), 7.06 (1H, d, J=8 Hz), 7.25 (1H, d, J=2 Hz), 7.34 (1H, d, J=8 Hz), 7.60 (1H, s), 7.96 (1H, s), 8.64 (1H, s), 11.01 (1H, s). MS, ES$^+$, m/z=449 for (M+H)$^+$. (Found: C, 57.59; H, 7.21; N, 12.43. $C_{27}H_{40}N_6$. $2.2C_2H_2O_4$. $0.5H_2O$ requires C, 57.51; H, 6.98; N, 12.82%).

EXAMPLE 12

N-[2-(1-Benzyl-2(RS)-piperidin-2-yl)ethyl]-N-[2-(5-(1,2,4-triazol-1-ylmethyl)-1H-indol-3-yl)ethyl]-N-methylamine Hydrogen Oxalate 1. 2-(1-t-Butyloxycarbonyl-2(RS)-piperidin-2-yl)ethanol 2-(2(RS)-Piperidin-2-yl)ethanol (4 g, 31 mmol) and di-t-butyldicarbonate (6.08 g, 28 mmol) were stirred in dichloromethane (100 ml) for 5 days, washed with 1M citric acid (50 ml), dried (sodium sulphate) and evaporated to afford the title compound as a gum (6.5 g, 92%). MS, ES$^+$, m/z=230 for (M+H)$^+$, $R_f$=0.70 in dichloromethane/methanol/ammonia (9:1:0.1) on silica plates.

2. N-[2-(1-t-Butyloxycarbonyl-2(RS)-piperidin-2-yl)ethyl]-N-[2-(5-(1,2,4-triazol-1-ylmethyl)-1H-indol-3-yl)ethyl]-N-methylamine A cooled (−78° C.), stirred solution of oxalyl chloride (1.37 ml, 15.7 mmol) in dichloromethane (45 ml) was treated dropwise with a solution of dimethyl sulphoxide (2.23 ml) in dichloromethane (15 ml), keeping the temperature below −65° C. After stirring at this temperature for 5 mins a solution of the foregoing alcohol (3 g, 13.1 mmol) in dichloromethane (60 ml) was added dropwise over 15 minutes. The reaction mixture was stirred at −70° for 20 minutes. Triethylamine (9.13 ml, 65.5 mmol) was added dropwise and the mixture was stirred at −70° C. for 10 minutes, allowed to warm to room temperature and treated with water (100 ml). The organic layer was separated, washed with water (100 ml), dried (sodium sulphate) then evaporated to afford the crude aldehyde as an oil. This aldehyde (534 mg, 2.35 mmol) in methanol (20 ml) was treated with N-methyl-N-[2-[5-(1,2,4-triazol-1-ylmethyl)-1H-indol-3-yl]ethyl]amine (300 mg, 1.18 mmol), glacial acetic acid (270 µl, 4.7 mmol) then sodium cyanoborohydride (148 mg, 2.35 mmol). Reaction mixture stirred at room temperature for 18 hours, basified using 10% potassium carbonate (30 ml) then the methanol evaporated. The aqueous residue was extracted with dichloromethane (4×50 ml). The combined organics were dried (sodium sulphate) then evaporated and the crude product purified by column chromatography on silica using dichloromethane/methanol/ammonia (9:1:0.1) to afford the title compound as a gum (240 mg, 44%). MS, ES$^+$, m/z=467 for (M+H)$^+$.

3. N-[2-(1-Benzyl-2(RS)-piperidin-2-yl)ethyl]-N-[2-(5-(1,2,4-triazol-1-ylmethyl)-1H-indol-3-yl)ethyl]-N-methylamine Hydrogen Oxalate The compound from the previous step (240 mg, 0.5 mmol) in dichloromethane (12 ml) was treated with trifluoroacetic acid (3 ml), and stirred at room temperature for 18 hours. The reaction mixture was evaporated then azeotroped with toluene (2×10 ml). This amine trifluoroacetate salt (0.25 mmol) was dissolved in methanol (10 ml), pH adjusted to 7 with sodium methoxide, then treated with benzaldehyde (30.4 µl, 0.3 mmol), glacial acetic acid (to pH=4) then sodium cyanoborohydride (19 mg, 0.3 mmol), stirred at room temperature for 18 hours. The reaction mixture was basified with 10% potassium carbonate (30 ml) then extracted with dichloromethane (5×50 ml). The organics were dried (sodium sulphate), evaporated and the crude product purified by column chromatography on silica using dichloromethane/methanol/ammonia (19:1:0.1) to afford the title compound free base (17 mg) as a gum. The hydrogen oxalate salt had mp>140° C. MS, ES⁺, m/z=457 for (M+H)⁺; δ (500 MHz, d₆-DMSO) 1.30–1.40 (1H, m), 1.42–1.46 (3H, m), 1.60–1.70 (1H, m), 1.70–1.80 (1H, m), 1.95–2.05 (1H, m), 2.05–2.20 (1H, m), 2.35–2.45 (1H, m), 2.75–2.90 (2H, m), 2.83 (3H, s), 3.06 (2H, t, J=8 Hz), 3.14 (2H, t, J=8 Hz), 3.30 (2H, t, J=8 Hz), 4.10–4.20 (2H, d, J=15 Hz), 5.57 (2H, s), 7.06 (1H, d, J=8 Hz), 7.27 (1H, d, J=2 Hz), 7.30–7.42 (6H, m), 7.59 (1H, s), 7.94 (1H, s), 8.60 (1H, s), 11.04 (1H, s). (Found: C, 57.72; H, 6.35; N, 12.59. $C_{28}H_{36}N_6$·2$C_2H_2O_4$·1.5$H_2O$ requires C, 57.91; H, 6.53; N, 12.66%).

EXAMPLE 13

N-[2-(1-Cyclohexylmethyl-2(RS)-piperidin-2-yl) ethyl]-N-[2-(5-(1,2,4-triazol-1-ylmethyl)-1H-indol-3-yl)ethyl]-N-methylamine Hydrogen Oxalate The title compound was prepared as described in Example 12, using cyclohexane carboxaldehyde instead of benzaldehyde in the final step. mp>170° C. (dec.). MS, ES⁺, m/z=463 for (M+H)⁺. (Found: C, 59.91; H, 7.62; N, 13.07. $C_{28}H_{42}N_6$·2$C_2H_2O_4$·0.1$H_2O$ requires C, 59.63; H, 7.23; N, 13.04%).

EXAMPLE 14

N-(1-Benzyl-(3R)-pyrrolidin-3-yl)-N-[2-(5-(1,2,4-triazol-1-ylmethyl)-1H-indol-3-yl)ethyl]-N-methylamine Hydrogen Oxalate a) (S)-3-Hydroxypyrrolidine-1-carboxylic acid tert-butyl ester A mixture of (S)-1-benzyl-3-pyrrolidinol (10.0 g, 56.4 mmol), di-tert-butyl dicarbonate (15.0 g, 69 mmol) in methanol (100 ml) and water (20 ml) was hydrogenated over palladium hydroxide (1 g) at 40 psi. After 3 hours the catalyst was removed by filtration through celite (washing with methanol). The filtrate was evaporated and the residue was purified by chromatography on silica gel, eluting with 80% ethyl acetate/hexane to afford the title alcohol (6.9 g, 65%) as a thick oil which solidified upon standing. δ (360 MHz, CDCl₃) 1.46 (9H, s, ᵗBu), 1.90–2.02 (2H, m), 2.44 (1H, br s, OH), 3.30–3.52 (4H, m, CH₂N), 4.44 (1H, m, CHOH).

b) (S)-3-Methanesulphonyloxypyrrolidine-1-carboxylic acid tert-butyl ester

Methanesulphonyl chloride (900 μl, 11.6 mmol) was added dropwise to a stirred solution of the alcohol from above (2.0 g, 10.7 mmol) and triethylamine (3.2 ml, 23 mmol) in dry THF (30 ml) at 0° C. under nitrogen. After 15 minutes at 0° C. the ice bath was removed and the reaction was stirred at room temperature for 1½ hours. The reaction was quenched with saturated aqueous sodium hydrogen carbonate. The aqueous was extracted with dichloromethane (×3). The combined extracts were dried (Na₂SO₄), filtered and evaporated. The residue was purified by chromatography on silica gel eluting with 2% MeOH/CH₂Cl₂ to afford the title mesylate (3 g, ~100%) as a thick oil. δ (360 MHz, CDCl₃), 1.47 (9H, s, ᵗBu), 2.08–2.38 (2H, br m), 3.05 (3H, s, CH₃), 3.44–3.74 (4H, m, CH₂N), 5.26 (1H, m, CHOMs).

c) (R)-3-3[N-Methyl-N-[2-(5-(1,2,4-triazol-1-ylmethyl)-1H-indol-3-yl)ethyl]amino]pyrrolidine-1-carboxylic acid tert-butyl ester A mixture of N-methyl-N-[2-(5-(1,2,4-triazol-1-ylmethyl)-1H-indol-3-yl)ethyl]amine (Example 2) (470 mg, 1.84 mmol), 4-methyl-2,6-di-tert-butylpyridine (1.03 g, 5.0 mmol) and the mesylate (from above) (650 mg, 2.79 mmol) in toluene (5 ml)/isopropyl alcohol (1 ml) was heated at 150° C. in a sealed tube for 20 hours. The reaction mixture was partitioned between CH₂Cl₂/H₂O. The aqueous was further extracted with CH₂Cl₂ (×2). The combined extracts were dried (Na₂SO₄), filtered and evaporated. The residue was purified by chromatography on silica gel, eluting with CH₂Cl₂/MeOH/NH₃ (95:5:0.5→91:8:1) to afford the title pyrrolidine (156 mg, 20%) as a foam. δ (360 MHz, CDCl₃) 1.46 (9H, s, ᵗBu), 1.76–1.84 (1H, m), 2.02–2.08 (1H, m), 2.38 (3H, s, CH₃), 2.72–2.78 (2H, m), 2.90–3.18 (4H, m), 3.22–3.32 (1H, m), 3.46–3.76 (3H, m), 5.43 (2H, s), 7.04–7.12 (2H, m, ArH), 7.34 (1H, d, J=8.4 Hz, ArH), 7.53 (1H, br s, ArH), 7.96 (1H, s, ArH), 8.01 (1H, m, ArH), 8.46 (1H, br s, NH), MS (ES⁺) m/e=425 [MH]⁺.

d) N-Methyl-N-(3(R)-pyrrolidin-3-yl)-N-[2-(5-(1,2,4-triazol-1-ylmethyl)-1H-indol-3-yl)ethyl]amine The N-tert-butoxycarbonylamine from above (150 mg, 0.35 mmol) was taken up in 90% formic acid (10 ml) at 0° C. After 30 minutes the ice bath was removed and the solution was stirred for a further 16 hours at room temperature. The formic acid was then removed in vacuo. The residue was partitioned between saturated aqueous potassium carbonate and n-butanol. The aqueous was further extracted with n-butanol (×2). The combined extracts were evaporated, and the residue was purified by chromatography on neutral alumina (grade III), eluting with 5% MeOH/CH₂Cl₂→CH₂Cl₂/MeOH/NH₃ 89:10:1 to afford the title amine (91 mg, 79%) as an oil. δ (360 MHz, CDCl₃) 1.62–1.74 (1H, m), 1.90–2.00 (1H, m), 2.38 (3H, s), 2.65–2.80 (3H, s, NCH₃), 2.65–2.80 (3H, m), 2.90–3.14 (6H, ;m), 5.43 (2H, s), 7.05 (1H, s, ArH), 7.10 (1H, dd, J=8.4, 1.4 Hz, ArH), 7.33 (1H, d, J=8.3 Hz, ArH), 7.53 (1H, s, ArH), 7.96 (1H, s, triazole-H), 8.00 (1H, s, triazole-H), 8.58 (1H, br s, NH).

e) N-(1-Benzyl-(3R)-pyrrolidin-3-yl)-N-[2-(5-(1,2,4-triazol-1-ylmethyl)-1H-indol-3-yl)ethyl]-N-methylamine Hydrogen Oxalate Sodium cyanoborohydride (45 mg, 0.72 mmol) was added in one portion to a stirred solution of the amine from above (91 mg, 0.28 mmol) and acetic acid (80 μl, 1.40 mmol) in dry methanol (10 ml) at room temperature under nitrogen. The mixture was cooled to 0° C., then benzaldehyde (40 μl, 0.39 mmol) was added. The reaction was stirred at 0° C. for 30 minutes, then at room temperature for a further 16 hours. The reaction was quenched with saturated aqueous potassium carbonate. The volatiles were removed in vacuo and the residue was partitioned between dichloromethane/water. The aqueous was further extracted with dichloromethane (×3). The combined extracts were dried (Na₂SO₄), filtered and evaporated. The residue was purified by chromatography on silica gel, eluting with CH₂Cl₂/MeOH/NH₃ 95:5:0.5→91:8:1 to give the title benzyl amine (103 mg, 98%) as a foam. The hydrogen oxalate was prepared (Et₂O/MeOH): (Found: C, 60.79; H, 6.02; N, 14.97. $C_{25}H_{30}N_6$·1.5($C_2H_2O_4$)·0.25$H_2O$ requires C, 60.69; H, 6.09; N, 15.17%), δ (360 MHz, d₆-DMSO) 1.94–2.06 (1H, m), 2.10–2.18 (1H, m), 2.54–2.60 (1H, m), 2.72 (3H, s, NCH₃), 2.80–2.94 (3H, m), 3.02–3.08 (2H, m), 3.12–3.20 (2H, m), 3.76 (2H, br s, CH₂Ph), 3.80–3.86 (1H, m), 5.44 (2H, s, CH₂-triazole), 7.08 (1H, d, J=8.4 Hz, ArH), 7.26 (1H, br s, ArH), 7.30–7.38 (6H, m, ArH), 7.57 (1H, s, ArH), 7.95 (1H, s, triazole-H), 8.62 (1H, s, triazole-H), 11.03 (1H, s, NH).

EXAMPLE 15

N-(1-Benzyl-(3S)-pyrrolidin-3-yl)-N-[2-(5-(1,2,4-triazol-1-ylmethyl)-1H-indol-3-yl)ethyl]-N-methylamine Hydrogen Oxalate a) (R)-3-Hydroxypyrrolidine-1-carboxylic acid tert-butyl ester Prepared as described in Example 14 from (R)-1-benzyl-3-pyrrolidinol.

b) (R)-3-Methanesulphonyloxypyrrolidine-1-carboxylic acid tert-butyl ester

Prepared as described in Example 14, using the above alcohol.

c) (S)-3-[N-Methyl-N-[2-(5-(1,2,4-triazol-1-ylmethyl)-1H-indol-3-yl)ethyl]amino]-pyrrolidine-1-carboxylic acid tert-butyl ester A mixture of the mesylate from above (500 mg, 1.88 mmol) and N-methyl-N-[2-(5-(1,2,4-triazol-1-ylmethyl)-1H-indol-3-yl)ethyl]amine (see Example 2) in isopropanol (3 ml) and toluene (10 ml) was heated at 150° C. in a sealed tube under nitrogen for 20 hours. Upon cooling the mixture was partitioned between dichloromethane and saturated aqueous sodium hydrogen carbonate. The aqueous was further extracted with dichloromethane (×3). The combined extracts were washed with brine (×1), then dried ($Na_2SO_4$), filtered and evaporated. The residue was purified by chromatography on silica gel, eluting with $CH_2Cl_2$/MeOH/$NH_3$ 95:5:0.5→91:8:1→89:10:1 to give the title amine (248 mg, 31%) as a foam, δ (360 MHz, $CDCl_3$) 1.46 (9H, s, $^t$Bu), 1.74–1.82 (1H, m), 2.02–2.08 (1H, m), 2.38 (3H, s, $NCH_3$), 2.70–2.78 (2H, m), 2.90–3.20 (4H, m), 3.22–3.32 (1H, m), 3.46–3.76 (3H, m), 5.44 (2H, s, $CH_2$-triazole), 7.04–7.12 (2H, m, ArH), 7.35 (1H, d, J=8.4 Hz, ArH), 7.53 (1H, s, ArH), 7.96 (1H, s, ArH), 8.01 (1H, m, ArH), 8.21 (1H, br s, NH), MS ($ES^+$) 425 $[MH]^+$.

d) N-Methyl-N-(3(S)-pyrrolidin-3-yl)-N-[2-(5-(1,2,4-triazol-1-ylmethyl)-1H-indol-3-yl)ethyl]amine The N-tert-butoxycarbonylamine (229 mg, 0.54 mmol) was taken up in 90% formic acid at 0° C. After 20 minutes at 0° C. the ice bath was removed and the mixture was stirred at room temperature for a further 16 hours. The formic acid was removed in vacuo and the residue was partitioned between saturated aqueous sodium hydrogen carbonate and n-butanol. The aqueous was further extracted with n-butanol (×2). The combined extracts were evaporated and the residue was purified by chromatography on neutral alumina (grade III) eluting with 5% MeOH/$CH_2Cl_2$→$CH_2Cl_2$/MeOH/$NH_3$ 89:10:1 to give the title amine (140 mg, 80%) as a thick oil; δ (360 MHz, $CDCl_3+d_4$MeOH) 1.62–1.74 (1H, m), 1.96–2.06 (1H, m), 2.40 (3H, s, $NCH_3$), 2.70–2.80 (3H, m), 2.88–3.12 (6H, m), 5.45 (2H, s, $CH_2$-triazole), 7.08–7.12 (2H, m, ArH), 7.38 (1H, d, J=8.3 Hz, ArH), 7.54 (1H, s, ArH), 7.95 (1H, s, triazole-H), 8.10 (1H, s, triazole-H), MS ($ES^+$) 325 $[MH]^+$.

e) N-(1-Benzyl-(3S)-pyrrolidin-3-yl)-N-[2-(5-(1,2,4-triazol-1-ylmethyl)-1H-indol-3-yl)ethyl]-N-methylamine Hydrogen Oxalate Sodium cyanoborohydride (66 mg, 10.5 mmol) was added in one portion to a stirred solution of the amine from above (135 mg, 0.42 mmol) and acetic acid (120 μl, 2.1 mmol) in dry methanol (15 ml) at room temperature under nitrogen. The mixture was cooled to 0° C. and benzaldehyde (55 μl, 0.54 mmol) was added. The reaction was stirred at 0° C. for 30 minutes, then at room temperature for 16 hours. The reaction was quenched with saturated aqueous potassium carbonate. The volatiles were removed in vacuo and the residue was partitioned between dichloromethane/water. The aqueous was further extracted with dichloromethane (×2). The combined extracts were washed with brine (×1), dried ($Na_2SO_4$), filtered and evaporated. The residue was purified by chromatography on silica gel, eluting with $CH_2Cl_2$/MeOH/$NH_3$ 95:5:0.5→91:8:1 to give the title benzyl amine (142 mg, 82%) as a foam. The hydrogen oxalate was prepared ($Et_2O$/MeOH): (Found: C, 59.89; H, 6.43; N, 14.43. $C_{25}H_{30}N_6$. 1.5($C_2H_2O_4$). 0.75$H_2O$. 0.1($C_4H_{10}O$) requires C, 59.79; H, 6.27; N, 14.73%), δ (360 MHz, $d_6$-DMSO) 1.94–2.04 (1H, m), 2.10–2.18 (1H, m), 2.54–2.60 (1H, m), 2.71 (3H, s, $NCH_3$), 2.78–2.92 (3H, m), 3.00–3.06 (2H, m), 3.12–3.18 (2H, m), 3.74 (2H, br s, $CH_2$Ph), 3.80–3.86 (1H, m), 5.43 (2H, s, $CH_2$-triazole), 7.07 (1H, d, J=8.4 Hz, ArH), 7.24 (1H, s, ArH), 7.30–7.38 (6H, m, ArH), 7.55 (1H, s, ArH), 7.94 (1H, s, triazole-H), 8.60 (1H, d, triazole-H), 11.01 (1H, br s, NH).

EXAMPLE 16

N-[1-(4-Fluorobenzyl)-(3R)-pyrrolidin-3-yl)-N-[2-(5-(1,2,4-triazol-1-ylmethyl)-1H-indol-3-yl)ethyl]-N-methylamine Hydrogen Oxalate Sodium cyanoborohydride (74 mg, 1.18 mmol) was added to a solution of the pyrrolidine (Example 14, step d, 153 mg, 0.47 mmol) and acetic acid (142 mg, 2.36 mmol) in dry methanol (25 ml) at room temperature under nitrogen. The mixture was cooled to 0° C., and 4-fluorobenzaldehyde (76 mg, 0.61 mmol) was added. After a further 30 minutes at 0° C. the reaction was stirred at room temperature for 16 hours. The reaction was quenched with saturated aqueous potassium carbonate. The volatiles were removed in vacuo and the residue was partitioned between dichloromethane/water. The aqueous was further extracted with dichloromethane (×3). The combined extracts were dried ($Na_2SO_4$), filtered and evaporated. The residue was purified by chromatography on silica gel, eluting with $CH_2Cl_2$/EtOH/$NH_3$ 70:8:1 to give the title benzyl amine (160 mg, 78%) as a foam. The hydrogen oxalate was prepared ($Et_2O$/MeOH). (Found: C, 53.13; H, 5.32; N, 11.53. $C_{25}H_{29}N_6F$. 3($C_2H_2O_4$). 0.1($H_2O$) requires C, 52.86; H, 5.04; N, 11.93%). δ (360 MHz, $D_2O$) 2.14–2.24 (1H, m), 2.56–2.66 (1H, m), 2.99 (3H, s, $NCH_3$), 3.26–3.30 (2H, m), 3.46–3.64 (5H, m), 3.72–3.78 (1H, m), 4.28–4.36 (1H, m), 4.38 (2H, br s, $CH_2$Ph—F), 5.54 (2H, br s, $CH_2$-triazole), 7.16–7.25 (3H, m, ArH), 7.35 (1H, s, ArH), 7.40–7.44 (2H, m, ArH), 7.52 (1H, d, J=8.4 Hz, ArH), 7.63 (1H, s, ArH), 8.15 (1H, s, triazole-H), 8.74 (1H, s, triazole-H); MS ($ES^+$) 433 $[MH]^+$.

EXAMPLE 17

N-[1-(4-Fluorobenzyl)-(3R)-pyrrolidin-3-yl]-N-methyl-N-[2-(5-(1,2,4-triazol-4-yl)-1H-indol-3-yl)ethyl]amine Hydrogen Oxalate a) (R)-3-(N-Benzyl-N-methylamino)pyrrolidine-1-carboxylic acid tert-butyl ester A mixture of (S)-3-methanesulphonyloxypyrrolidine-1-carboxylic acid tert-butyl ester (Example 14) (2.43 g, 9.2 mmol) and N-benzyl-N-methylamine (3.5 g, 27 mmol) was stirred and heated at 100° C. for 3 hours, under nitrogen. The N-benzyl-N-methylamine was removed in vacuo, and the residue was partitioned between dichloromethane/water. The aqueous was further extracted with dichloromethane (×1). The combined extracts were washed with brine (×2), dried ($Na_2SO_4$) filtered and evaporated. The residue was purified by chromatography on silica gel, eluting with 20% ethyl acetate/hexane to afford the title amine (1.64 g, 61%) as an oil; δ (250 MHz, $CDCl_3$) 1.46 (9H, s, $^t$Bu), 1.80–2.05 (2H, m), 2.10 (3H, s, $NCH_3$), 2.95–3.80 (7H, m), 7.24–7.34 (5H, m, ArH).

b) (R)-3-Methylaminopyrrolidine-1-carboxylic acid tert-butyl ester

A mixture of the N-benzyl-N-methylamine from above (4.7 g, 16.1 mmol), ammonium formate (5.3 g, 84 mmol), and 10% Pd/C (1.2 g) in methanol (100 ml) was stirred and heated at reflux for 1.75 hours under nitrogen. Upon cooling the catalyst was removed by filtration through celite, washing with methanol. The filtrate was evaporated and the residue was partitioned between dichloromethane and saturated aqueous sodium hydrogen carbonate. The aqueous was further extracted with dichloromethane (×2). The combined extracts were dried ($Na_2SO_4$), filtered and evaporated. The residue was purified by chromatography on silica gel, eluting with $CH_2Cl_2$/MeOH/$NH_3$ 95:5:0.5→93:6:1→91:8:1 to afford the title amine (3.0 g, 93%) as an oil; δ (250 MHz, $CDCl_3$) 1.46 (9H, s, $^tBu$), 1.64–1.78 (1H, m), 1.98–2.10 (1H, m), 2.44 (3H, s, $NCH_3$), 3.04–3.60 (5H, m).

c) (R)-3-[N-Methyl-N-[2-(5-(1,2,4-triazol-4-yl)-1H-indol-3-yl)ethyl]amino]pyrrolidine-1-carboxylic acid tert-butyl ester Sodium iodide (300 mg, 2.0 mmol) was added to a stirred solution/suspension of methanesulphonic acid 2-[5-(1,2,4-triazol-4-yl)-1H-indol-3-yl]ethyl ester (prepared from the corresponding alcohol, WO 95/32196) (600 mg, 2.0 mmol), (R)-3-methylaminopyrrolidine-1-carboxylic acid tert-butyl ester (600 mg, 3.0 mmol) and potassium carbonate (830 mg, 6.0 mmol) in dry isopropanol (50 ml) at room temperature under nitrogen. The mixture was stirred and heated at reflux, protected from light for 20 hours. Upon cooling, the volatiles were removed in vacuo. The residue was partitioned between dichloromethane/water. The aqueous was further extracted with dichloromethane (×2). The combined extracts were dried ($Na_2SO_4$), filtered and evaporated. The residue was purified by chromatography on silica gel, eluting with $CH_2Cl_2$/MeOH/$NH_3$ 95:5:0.5→93:6:1→91:8:1 to give the title tryptamine (770 mg) as a thick gum. ($^1H$ nmr indicated contamination with the pyrrolidine-amine. Corrected yield of desired product≈60%≈500 mg). δ (360 MHz, $CDCl_3$+$d_4$MeOH) 1.46 (9H, s, $^tBu$), 1.70–1.85 (1H, m), 2.05–2.15 (1H, m), 2.42 (3H, s, $NCH_3$), 2.75–3.60 (9H, m), 7.17 (1H, d, J=8.7 Hz, ArH), 7.22 (1H, s, ArH), 7.52 (1H, d, J=8.6 Hz, ArH), 7.60 (1H, s, ArH), 8.62 (2H, br s, triazole-H); MS ($ES^+$) 411 $[MH]^+$.

d) N-Methyl-N-(3(R)-pyrrolidin-3-yl)-N-[2-(5-(1,2,4-triazol-4-yl)-1H-indol-3-yl)ethyl]amine The crude N-tert-butoxycarbonylpyrrolidine from above (770 mg) was taken up in 90% formic acid (30 ml) at 0° C. After 20 minutes the cooling bath was removed and the mixture was stirred at room temperature for 16 hours. The formic acid was removed in vacuo. The residue was partitioned between n-butanol and saturated aqueous sodium hydrogen carbonate. The aqueous was further extracted with n-butanol (×6). The combined extracts were evaporated. The residue was purified by chromatography on neutral alumina (grade III), eluting with 5% MeOH/$CH_2Cl_2$→$CH_2Cl_2$/MeOH/$NH_3$ 89:10:1 to give the title amine (354 mg, 58% for 2 steps); δ (250 MHz, $CDCl_3$+$d_4$MeOH) 1.66–1.74 (1H, m), 1.98–2.06 (1H, m), 2.40 (3H, s, $NCH_3$), 2.70–2.80 (3H, m), 2.90–3.16 (6H, m), 7.15 (1H, dd, J=8.5, 2.3 Hz, ArH), 7.21 (1H, s, ArH), 7.50 (1H, d, J=8.4 Hz), 7.57 (1H, d, J=1.9 Hz), 8.56 (2H, s, triazole-H); MS ($ES^+$) 311 $[MH]^+$.

e) N-[1-(4-Fluorobenzyl)-(3R)-pyrrolidin-3-yl]-N-methyl-N-[2-(5-(1,2,4-triazol-4-yl)-1H-indol-3-yl)ethyl]amine Hydrogen Oxalate Sodium cyanoborohydride (85 mg, 1.35 mmol) was added in one portion to a stirred solution of the amine from above (166 mg, 0.53 mmol) and acetic acid (150 μl, 2.62 mmol) in dry methanol (20 ml) at room temperature under nitrogen. The mixture was cooled to 0° C. and 4-fluorobenzaldehyde (75 μl, 0.70 mmol) was added. The mixture was stirred at 0° C. for a further 20 minutes, then at room temperature for 16 hours. The reaction was quenched with saturated aqueous potassium carbonate. The volatiles were removed in vacuo and the residue was partitioned between dichloromethane/water. The aqueous was further extracted with dichloromethane (×2). The combined extracts were dried ($Na_2SO_4$), filtered and evaporated. The residue was purified by chromatography on silica gel, eluting with $CH_2Cl_2$/MeOH/$NH_3$ 95:5:0.5→89:10:1 to give the title benzyl amine (138 mg, 62%) as a foam. The hydrogen oxalate was prepared ($Et_2O$/MeOH). (Found: C, 59.14; H, 5.73; N, 15.27. $C_{24}H_{27}FN_6$. $1.1(C_2H_2O_4)$. $H_2O$. $0.1(C_4H_{10}O)$ requires C, 58.84; H, 5.98; N, 15.48%). δ (360 MHz, $d_6$-DMSO) (part of spectrum obscured by HOD) 1.98–2.06 (1H, m), 2.08–2.18 (1H, m), 2.70–2.94 (7H, m), 3.04–3.22 (4H, m), 3.68 (2H, br s, $CH_2Ph$—F), 7.13 (2H, app t, J=8.9 Hz, ArH), 7.32–7.35 (3H, m, ArH), 7.36 (1H, s, ArH), 7.52 (1H, d, J=8.6 Hz, ArH), 7.86 (1H, s, ArH), 9.01 (2H, s, triazole-H), 11.26 (1H, br s, N—H); MS ($ES^+$) 419 $[MH]^+$.

EXAMPLE 18

N-(1-Benzylpiperidin-4-yl)-N-[2-(5-(1,2,4-triazol-4-yl)-1H-indol-3-yl)ethyl]-N-methylamine Hydrogen Oxalate 1. N-(1-Benzylpiperidin-4-yl)-N-[2-(5-(1,2,4-triazol-4-yl)-1H-indol-3-yl)ethyl]amine Hydrogen Oxalate 4-(1,2,4-Triazol-4-yl)phenylhydrazine (3 g, 17.12 mmol) and 4-chlorobutyraldehyde dimethyl acetal (2.35 g, 15.41 mmol) were heated at reflux in ethanol/water (5:1, 120 ml) in the presence of concentrated hydrochloric acid (3.77 ml) under nitrogen for 6 hours. The volatiles were evaporated and the residue partitioned between 2M sodium hydroxide (50 ml) and n-butanol.

The organic layer was separated and the solvent evaporated. The crude product was purified by column chromatography on silica using dichloromethane/methanol/ammonia (40:8:1) to give 2-[5-(1,2,4-triazol-4-yl)-1H-indol-3-yl]ethylamine as a brown oil (1.9 g, 49%). This tryptamine (1.0 g, 4.4 mmol), 1-benzylpiperidin-4-one (874 mg, 4.6 mmol), glacial acetic acid (1.58 g, 26.4 mmol) and sodium cyanoborohydride (290 mg, 4.6 mmol) were stirred in methanol (75 ml) at room temperature for 18 hours. The mixture was treated with 2M sodium hydroxide (to pH=8), evaporated and the aqueous partitioned between 2M sodium hydroxide (30 ml) and ethyl acetate (50 ml). The organic layer was separated and the aqueous re-extracted with ethyl acetate (2×50 ml). The combined organics were washed with saturated sodium chloride solution (2×30 ml), dried (sodium sulphate) and evaporated. The crude product was purified by column chromatography on silica using dichloromethane/methanol/ammonia (10:1:0.1) to afford the title compound free base as a solid (1.4 g, 79%). The hydrogen oxalate salt had mp 187–189° C., MS, $ES^+$, m/z=401 for $(M+H)^+$. (Found: C, 56.11; H, 5.88; N, 14.08. $C_{24}H_{28}N_6$. $2C_2H_2O_4$. $H_2O$ requires C, 56.18; H, 5.72; N, 14.04%).

2. N-(1-Benzylpiperidin-4-yl)-N-[2-(5-(1,2,4-triazol-4-yl)-1H-indol-3-yl)ethyl]-N-methylamine Hydrogen Oxalate The foregoing amine (545 mg, 1.36 mmol), glacial acetic acid (468 μl, 8.16 mmol) and sodium cyanoborohydride (94 mg, 1.5 mmol) in methanol (50 ml) were treated with formaldehyde (36% in water, 109 μl. 1.5 mmol) and the mixture stirred at room temperature for 3 hours then quenched with 2M sodium hydroxide (5 ml). The volatiles were evaporated and the residue partitioned between 2M sodium hydroxide and ethyl acetate. The organic layer was washed with saturated sodium chloride solution, dried (sodium sulphate) then evaporated. The crude product was purified by column chromatography on silica using dichloromethane/methanol/ammonia (9:1:0.1) to afford the title compound free base as a pale yellow foam (513 mg, 91%). The hydrogen oxalate salt had mp 202–204° C. MS, ES$^+$, m/z=415 for (M+H)$^+$. (Found: C, 59.11; H, 6.45; N, 14.88. $C_{25}H_{30}N_6$. $1.5C_2H_2O_4$. $H_2O$ requires C, 59.25; H, 6.21; N, 14.81%).

What is claimed is:

1. A compound of formula I, or a pharmaceutically acceptable salt or prodrug thereof:

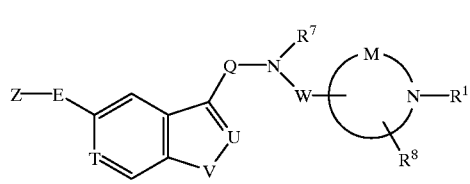
(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (a), (b), (c) or (d):

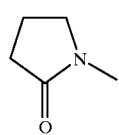
(a)

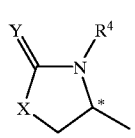
(b)

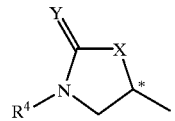
(c)

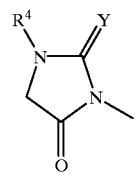
(d)

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 4 carbon atoms, optionally substituted in any position by one or more substituents selected from fluoro and hydroxy;

T represents nitrogen or CH;

U represents nitrogen or C—R$^2$;

V represents oxygen, sulphur or N—R$^3$;

W represents a chemical bond or a straight or branched alkylene chain containing from 1 to 4 carbon atoms;

M represents the residue of an azetidine, pyrrolidine or piperidine ring;

R$^1$ represents C$_{3-7}$ cycloalkyl(C$_{1-6}$)alkyl, aryl(C$_{1-6}$)alkyl or heteroaryl(C$_{1-6}$)alkyl, any of which groups may be optionally substituted;

R$^2$, R$^3$, R$^4$ and R$^7$ independently represent hydrogen or C$_{1-6}$ alkyl; with the proviso that when M represents the residue of an azetidine or pyrrolidine ring, Q is methylene, W represents a chemical bond, R$^7$ is C$_{1-6}$ alkyl R$^5$ and R$^6$ independently represent hydrogen, C$_{1-6}$ alkyl, trifluoromethyl, phenyl, methylphenyl, or an optionally substituted aryl(C$_{1-6}$)alkyl or heteroaryl(C$_{1-6}$)alkyl group; or R$^5$ and R$^6$, when linked through a nitrogen atom, together represent the residue of an optionally substituted azetidine, pyrrolidine, piperidine, morpholine or piperazine ring; and R$^8$ represents hydrogen or hydroxy.

2. A compound as claimed in claim 1 represented by formula II, and pharmaceutically acceptable salts and prodrugs thereof:

(II)

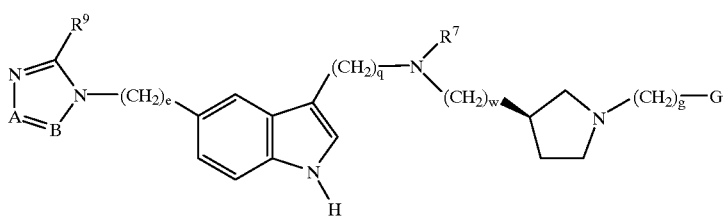

wherein
e is zero, 1, 2 or 3;
g is 1, 2 or 3;
q is 2, 3 or 4;
w is zero, 1 or 2;
A represents nitrogen or CH;
B represents nitrogen or C—$R^{10}$;
$R^9$ and $R^{10}$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;
G represents a group of formula (Ga), (Gb), (Gc) or (Gd):

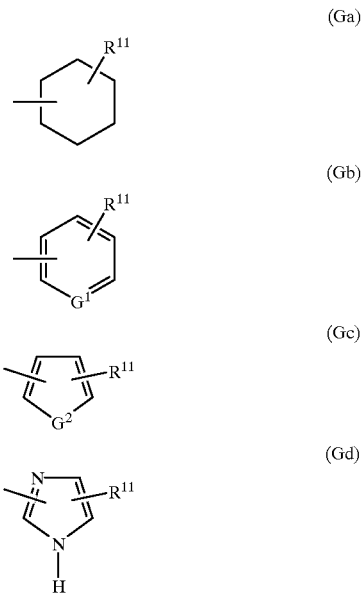

in which
$G^1$ represents CH or nitrogen;
$G^2$ represents oxygen, sulphur, NH or N-methyl; and
$R^{11}$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$) alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

3. A compound as claimed in claim 2 wherein $R^{11}$ represents hydrogen, fluoro, chloro or trifluoromethyl.

4. A compound as claimed in claim 2 or claim 3 wherein G represents a group of formula (Ga).

5. A compound as claimed in any one of claims 2 to 4 wherein G represents a group of formula (Gb) in which $G^1$ represents CH.

6. A compound selected from:
1-benzyl-3-[N-ethyl-N-[2-(5-(1,2,4-triazol-1-ylmethyl)-1H-indol-3-yl)ethyl]amino]methylazetidine;
1-cyclohexylmethyl-3-[N-methyl-N-[2-(5-(1,2,4-triazol-1-ylmethyl)-1H-indol-3-yl)ethyl]amino]methylazetidine;
1-benzyl-3-[N-methyl-N-[2-(5-(1,2,4-triazol-1-ylmethyl)-1H-indol-3-yl)ethyl]amino]methylazetidine;
1-(2-chlorobenzyl)-3-[N-methyl-N-[2-(5-(1,2,4-triazol-1-ylmethyl)-1H-indol-3-yl)ethyl]amino]methylazetidine;
1-(4-fluorobenzyl)-3-[N-methyl-N-[2-(5-(1,2,4-triazol-1-ylmethyl)-1H-indol-3-yl)ethyl]amino]methylazetidine;
1-(2-trifluoromethylbenzyl)-3-[N-methyl-N-[2-(5-(1,2,4-triazol-1-ylmethyl)-1H-indol-3-ylethyl]amino]methylazetidine;
1-(2-chloro-6-fluorobenzyl)-3-[N-methyl-N-[2-(5-(1,2,4-triazol-1-ylmethyl)-1H-indol-3-yl)ethyl]amino]methylazetidine;
1-benzyl-3-hydroxy-3-[N-methyl-N-[2-(5-(1,2,4-triazol-1-ylmethyl)-1H-indol-3-yl)ethyl]amino]methylazetidine;
1-benzyl-3-[N-methyl-N-[2-(5-(1,2,4-triazol-1-ylmethyl)-1H-indol-3-yl)ethyl]amino]methylpyrrolidine;
1-benzyl-3-[N-methyl-N-[2-(5-(1,2,4-triazol-1-ylmethyl)-1H-indol-3-yl)ethyl]amino]methylpiperidine;
1-cyclohexylmethyl-3-[N-methyl-N-[2-(5-(1,2,4-triazol-1-ylmethyl)-1H-indol-3-yl)ethyl]amino]methylpiperidine;
1-benzyl-2-[2-[N-methyl-N-[2-(5-(1,2,4-triazol-1-ylmethyl)-1H-indol-3-yl)ethyl]amino]ethyl]piperidine;
1-cyclohexylmethyl-2-[2-[N-methyl-N-[2-(5-(1,2,4-triazol-1-ylmethyl)-1H-indol-3-yl)ethyl]amino]ethyl]piperidine;
1-benzyl-3-(R)-[N-methyl-N-[2-(5-(1,2,4-triazol-1-ylmethyl)-1H-indol-3-yl)ethyl]amino]pyrrolidine;
1-benzyl-3-(S)-[N-methyl-N-[2-(5-(1,2,4-triazol-1-ylmethyl)-1H-indol-3-yl)ethyl]amino]pyrrolidine;
1-(4-fluorobenzyl)-3-(R)-[N-methyl-N-[2-(5-(1,2,4-triazol-1-ylmethyl)-1H-indol-3-yl)ethyl]amino]pyrrolidine;
1-(4-fluorobenzyl)-3-(R)-[N-methyl-N-[2-(5-(1,2,4-triazol-4-yl)-1H-indol-3-yl)ethyl]amino]pyrrolidine;
1-benzyl-4-[N-methyl-N-[2-(5-(1,2,4-triazol-4-yl)-1H-indol-3-yl)ethyl]amino]piperidine;
and pharmaceutically acceptable salts and prodrugs thereof.

7. A pharmaceutical composition comprising a therapeutically effective amount of a compound of formula I as defined in claim 1 or a pharmaceutically acceptable salt thereof or a prodrug thereof in association with a pharmaceutically acceptable carrier.

8. A method for the treatment of migraine, cluster headache, chronic paroxysmal hemicrania, headache associated with vascular disorders, tension headache, and pediatric migraine, which method comprises administering to a patient in need of such treatment an effective amount of a compound of formula I as defined in claim 1 or a pharmaceutically acceptable salt or a prodrug thereof.

9. A process for the preparation of a compound as claimed in claim 1, which comprises:

(A) attachment of the R¹ moiety to a compound of formula III:

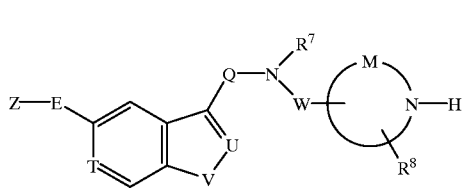
(III)

wherein Z, E, Q, T, U, V, W, M, R⁷ and R⁸ are as defined in claim 1; or (B) reacting a compound of formula IV:

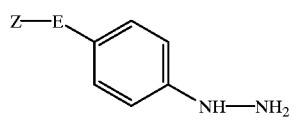
(IV)

wherein Z and E are as defined in claim 1; with a compound of formula IX, or a carbonyl-protected form thereof:

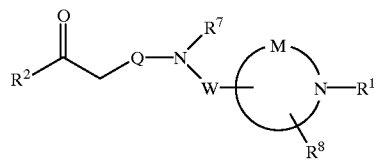
(IX)

wherein Q, W, M, R¹, R², R⁷ and R⁸ are as defined in claim 1; followed, where required, by N-alkylation by standard methods to introduce the moiety R³; or (C) reacting a compound of formula XI:

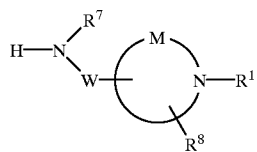
(XI)

wherein W, M, R¹, R⁷ and R⁸ are as defined in claim 1; with a compound of formula XII:

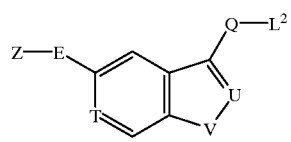
(XII)

wherein Z, E, Q, T, U and V are as defined in claim 1, and L² represents a suitable leaving group; or (D) cyclising a compound of formula XIV:

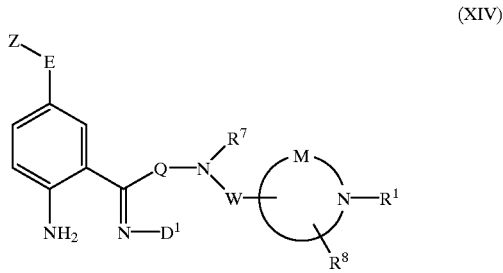
(XIV)

in which Z, E, Q, W, M, R¹, R⁷ and R⁸ are as defined in claim 1, and D¹ represents a readily displaceable group; followed, where required, by N-alkylation by standard methods to introduce the moiety R³; or (E) cyclising a compound of formula XVIII:

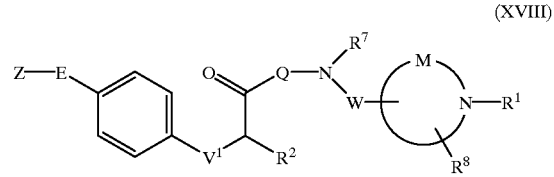
(XVIII)

wherein Z, E, Q, W, M, R¹, R², R⁷ and R⁸ are as defined in claim 1, and V¹ represents oxygen or sulphur; or (F) reducing a compound of formula XXII:

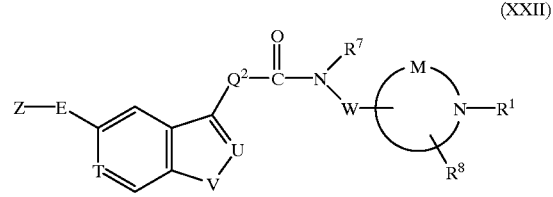
(XXII)

wherein Z, E, T, U, V, W, M, R¹, R⁷ and R⁸ are as defined in claim 1, and —Q²—CH₂— corresponds to the moiety Q as defined in claim 1; or (G) reacting a compound of formula XXV:

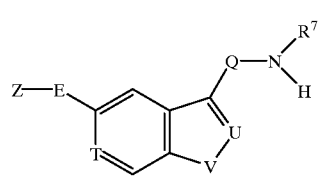
(XXV)

wherein Z, E, Q, T, U, V and R⁷ are as defined in claim 1; with a compound of formula XXVII:

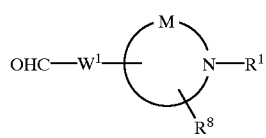

(XXVII)

wherein M, $R^1$ and $R^8$ are as defined in claim 1, and —$CH_2$—$W^1$— corresponds to the moiety W as defined in claim 1; in the presence of a reducing agent; or (H) reacting a compound of formula XXV as defined above with a compound of formula XXIX:

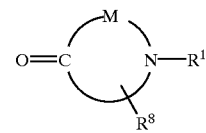

(XXIX)

wherein M, $R^1$ and $R^8$ are as defined above; in the presence of a reducing agent; and (J) if required, converting a compound of formula I initially obtained into a further compound of formula I by conventional methods.

* * * * *